(12) United States Patent  (10) Patent No.: US 8,088,901 B2
Morishita et al.  (45) Date of Patent: Jan. 3, 2012

(54) AZAINDENOFLUORENEDIONE DERIVATIVE, MATERIAL FOR ORGANIC ELECTROLUMINESCENCE DEVICE AND ORGANIC ELECTROLUMINESCENCE DEVICE

(75) Inventors: Hironobu Morishita, Sodegaura (JP); Yuichiro Kawamura, Sodegaura (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 414 days.

(21) Appl. No.: 12/325,052

(22) Filed: Nov. 28, 2008

(65) Prior Publication Data

US 2009/0315022 A1  Dec. 24, 2009

(30) Foreign Application Priority Data

Nov. 30, 2007  (JP) .................................. 2007-309941

(51) Int. Cl.
 *C07D 487/00*  (2006.01)
(52) U.S. Cl. ........................ 532/1; 257/40; 257/E51.001
(58) Field of Classification Search .................... 257/40, 257/E51.001; 532/1
 See application file for complete search history.

(56) References Cited

U.S. PATENT DOCUMENTS 6,597,012 B2  7/2003 Kido et al.
7,074,500 B2  7/2006 Pfeiffer et al.
  (Continued)

FOREIGN PATENT DOCUMENTS

JP  2001-297883  10/2001
  (Continued)

OTHER PUBLICATIONS

U.S. Appl. No. 12/519,170, filed Jun. 15, 2009, Morishita.
U.S. Appl. No. 13/132,141, filed Jun. 1, 2011, Morishita, et al.

*Primary Examiner* — Kenneth Parker
*Assistant Examiner* — Anthony Ho
(74) *Attorney, Agent, or Firm* — Oblon, Spivak, McClelland, Maier & Neustadt, L.L.P.

(57) ABSTRACT

An azaindenofluorenedione derivative shown by the following formula (I), (IIa) or (IIb):

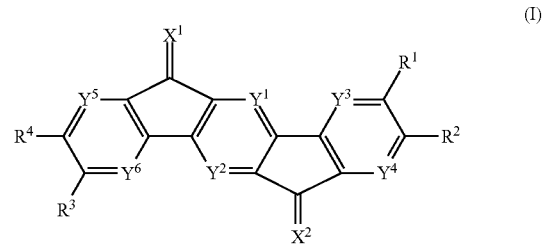

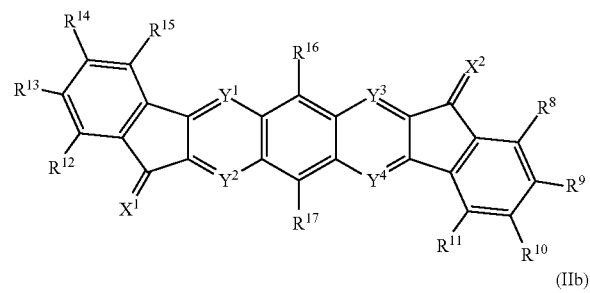

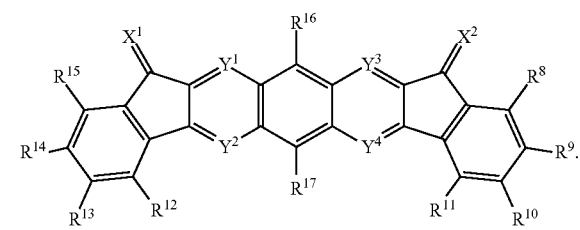

12 Claims, 1 Drawing Sheet

U.S. PATENT DOCUMENTS

| | | |
|---|---|---|
| 7,638,206 B2 * | 12/2009 | Coggan et al. ............... 428/690 |
| 2002/0132134 A1 * | 9/2002 | Hu et al. ...................... 428/690 |
| 2005/0255334 A1 | 11/2005 | Kang et al. |
| 2009/0036643 A1 * | 2/2009 | Marks et al. ................. 528/380 |

FOREIGN PATENT DOCUMENTS

| | | |
|---|---|---|
| JP | 2003-31365 | 1/2003 |
| JP | 2004-514257 | 5/2004 |
| WO | WO 2006065105 A1 * | 6/2006 |

* cited by examiner

(12) United States Patent

AZAINDENOFLUORENEDIONE DERIVATIVE, MATERIAL FOR ORGANIC ELECTROLUMINESCENCE DEVICE AND ORGANIC ELECTROLUMINESCENCE DEVICE

TECHNICAL FIELD

The invention relates to a novel azaindenofluorenedione derivative, a material for an organic electroluminescence device and an organic electroluminescence device using the same.

BACKGROUND ART

An organic electroluminescence device (hereinafter the term "electroluminescence" is often abbreviated as "EL") is a self-emission device utilizing the principle that a fluorescent substance emits light by the recombination energy of holes injected from an anode and electrons injected from a cathode when an electric field is impressed.

As the stack structure of the organic EL device, a two-layered type of a hole-transporting (injecting) layer and an electron-transporting emitting layer, a three-layered type of a hole-transporting (injecting) layer, an emitting layer and an electron-transporting (injecting) layer, or the like, are widely known. In such stack structure devices, their device structures and fabrication methods have been contrived to increase recombination efficiency of injected holes and electrons.

As the hole-transporting material used in an organic EL device, aromatic diamine derivatives or aromatic condensed ring diamine derivatives have heretofore been known.

However, in the case of an organic EL device using these aromatic diamine derivatives as the hole-transporting material, since an increased applied voltage is required to obtain sufficient luminance, problems such as a shortened device life or increased power consumption occur.

In order to solve the above-mentioned problems, doping of an electron-accepting compound such as a Lewis acid to a hole-injecting layer of an organic EL device has been proposed (Patent Documents 1 to 4 or the like). However, the electron-accepting compounds used in Patent Documents 1 to 4 have problems that they are unstable in handling during the production of an organic EL device, they shorten the life of an organic EL device due to the lack of stability such as heat resistance during driving of the organic EL device, or the like.

Tetrafluorotetracyanoquinodimethane (TCNQF$_4$) exemplified as an electron-accepting compound in Patent Documents 3, 4 or the like has a high sublimation property since it has a small molecular weight and is substituted with fluorine. Therefore, when an organic EL device is fabricated by vacuum vapor deposition using this compound, the compound may diffuse within a deposition apparatus, and contaminate the apparatus and the device.

Patent Document 1: JP-A-2003-031365
Patent Document 2: JP-A-2001-297883
Patent Document 3: JP-T-2004-514257
Patent Document 4: US2005/0255334A1

The invention has been made in view of the above-mentioned problem, and an object thereof is to provide an electron-accepting material suitable for use as a constitution material of an organic EL device.

DISCLOSURE OF THE INVENTION

As a result of intensive studies, the inventors noted the skeleton of azaindenofluorenedione. These compounds have two quinone sites ("=X$^1$, =X$^2$" in formula (I), for example) in a molecule. By converting the two quinone sites to a dicyanomethylene group, a cyanoimino group or the like, these compounds have an electron acceptability which is significantly larger than that of a fluorenone derivative. Furthermore, due to the presence of a nitrogen-containing ring in the same molecule, electron acceptability is increased.

In addition, due to the small molecular weight or the presence of only one quinone site, a fluorene derivative has a low sublimation temperature and hence, may contaminate an apparatus during deposition for film formation. On the other hand, due to the bonding of five or more aromatic rings or heterocyclic rings, an azaindenofluorenedione derivative is improved in heat resistance and capable of fabricating an organic EL device by deposition since it can retain an appropriate deposition temperature. In addition, by converting two quinone sites within the molecule into a dicyanomethylene group, a cyanoimino group or the like, crystallization can be suppressed.

Furthermore, by introducing a specific substituent into a terminal ring, electron acceptability can be further enhanced or crystallization can be further suppressed.

The inventors have found that, by using an azaindenofluorenedione derivative, which has the above-mentioned characteristics, in an organic EL device, in particular, in a hole-injecting layer, driving voltage can be lowered or the device life can be prolonged.

The invention can provide the following azaindenofluorenedione derivative or the like.
1. An azaindenofluorenedione derivative shown by the following formula (I), (IIa) or (IIb):

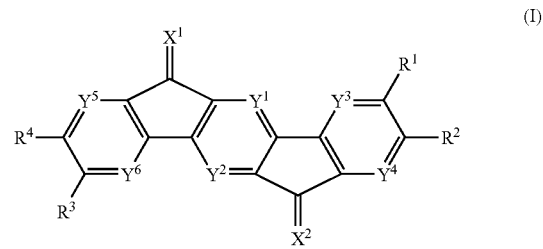

wherein X$^1$ and X$^2$, which may be the same or different, are one of the following divalent groups (a) to (g); Y$^1$ and Y$^2$ are independently —N= or —CH=, Y$^3$ to Y$^6$ are independently —N= or —CR= and at least one of Y$^1$ to Y$^6$ is —N=; R$^1$ to R$^4$ and R, which may be the same or different, are a hydrogen atom, substituted or unsubstituted alkyl group, substituted or unsubstituted aryl group, substituted or unsubstituted heterocyclic group, halogen atom, substituted or unsubstituted alkoxy group, substituted or unsubstituted aryloxy group or cyano group; and R$^1$ and R$^2$, or R$^3$ and R$^4$ may be bonded to each other to form a ring, respectively;

-continued

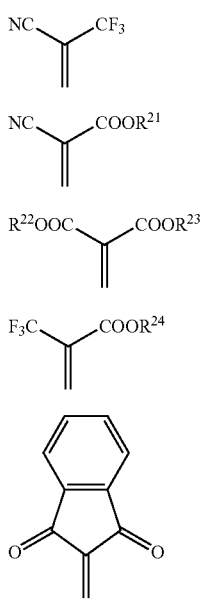

wherein $R^{21}$ to $R^{24}$, which may be the same or different, are a hydrogen atom, substituted or unsubstituted alkyl group, substituted or unsubstituted aryl group, or substituted or unsubstituted heterocyclic group; and $R^{22}$ and $R^{23}$ may be bonded to each other to form a ring;

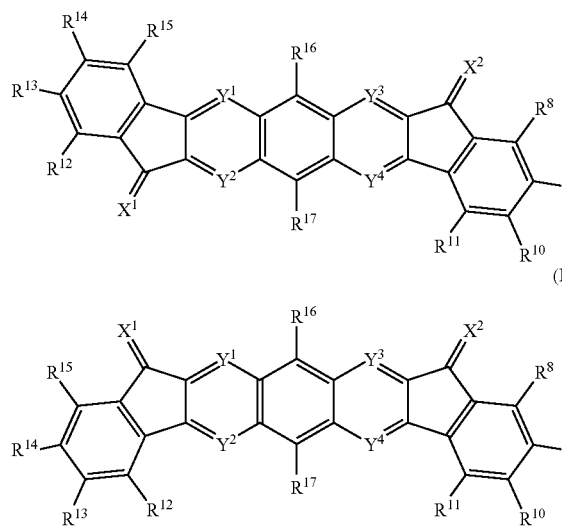

wherein $X^1$ and $X^2$ are the same as $X^1$ and $X^2$ in the formula (I); $Y^1$ to $Y^4$ are independently —N= or —CH=, and at least one of $Y^1$ to $Y^4$ is —N=; $R^8$ to $R^{17}$, which may be the same or different, a hydrogen atom, substituted or unsubstituted alkyl group, substituted or unsubstituted aryl group, substituted or unsubstituted heterocyclic group, halogen atom, substituted or unsubstituted alkoxy group, substituted or unsubstituted aryloxy group or cyano group; and adjacent groups of $R^8$ to $R^{11}$ or $R^{12}$ to $R^{15}$ may be bonded to each other to form a ring.

2. A material for an organic electroluminescence device comprising the azaindenofluorenedione derivative of 1.

3. The material for an organic electroluminescence device of 2, which has a reduction potential of −1.0V (vsFc⁺/Fc; Fc indicates ferrocene) or more in an acetonitrile solution.

4. The material for an organic electroluminescent device of 2 or 3, which is a hole-injecting material.

5. An organic electroluminescence device comprising an anode, a cathode and an organic thin film layer therebetween;

the organic thin film layer being a multilayer stack wherein a hole-injecting layer, a hole-transporting layer, an emitting layer and an electron-transporting layer are stacked in this order from the anode; and the hole-injecting layer containing the material for an organic electroluminescence device of 2 or 3.

According to the invention, a novel material for an organic EL device can be provided. In addition, the invention can provide an organic EL device which can be driven at a low voltage and has a long life.

BEST MODE FOR CARRYING OUT THE INVENTION

Figure 1:
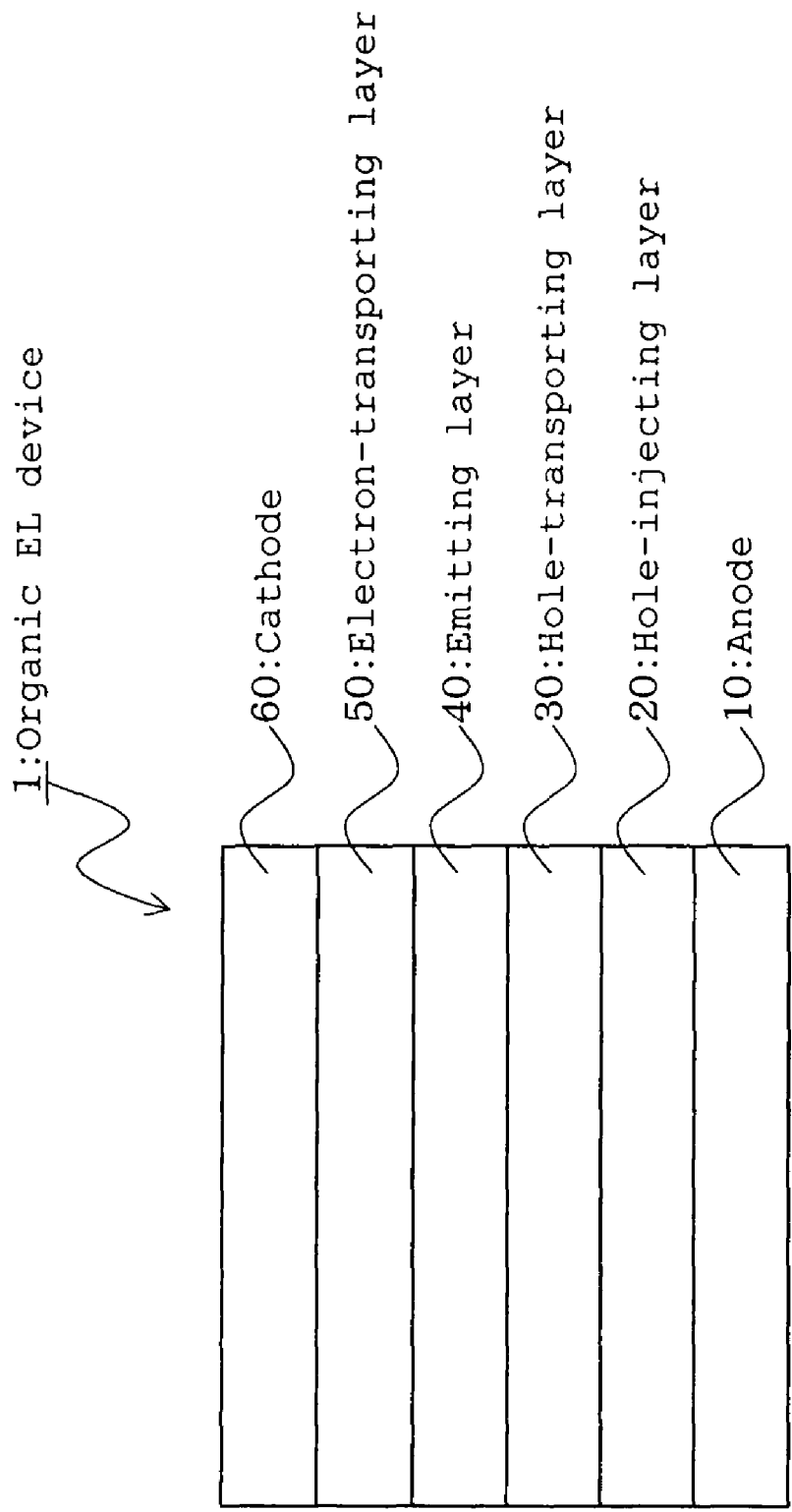
FIG. 1 is a schematic cross-sectional view showing one embodiment of the organic EL device according to the invention.

The azaindenofluorenedione derivative of the invention can be shown by the following formula (I), (IIa) or (IIb):

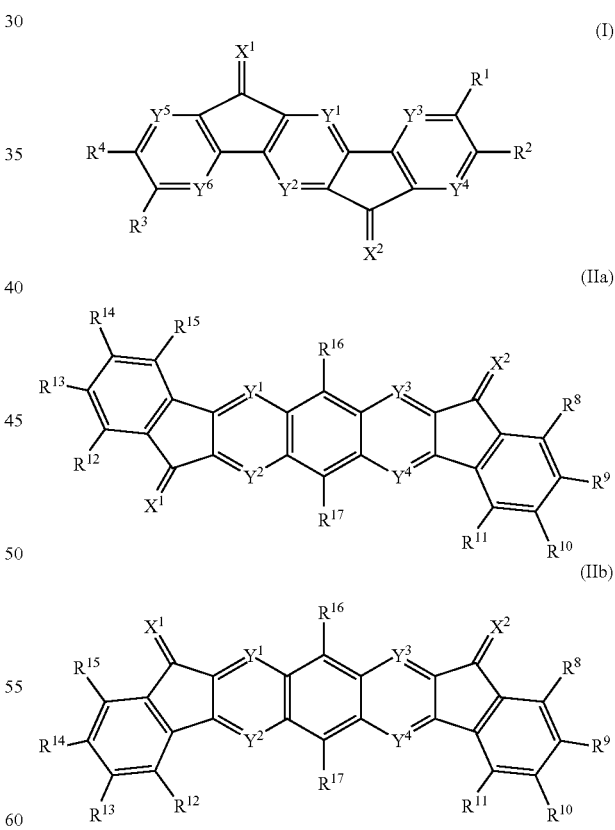

In the above formula, $R^1$ to $R^4$ and $R^8$ to $R^{17}$ are a hydrogen atom, substituted or unsubstituted alkyl group, substituted or unsubstituted aryl group, substituted or unsubstituted heterocyclic group, halogen atom, substituted or unsubstituted alkoxy group, substituted or unsubstituted aryloxy group or cyano group.

Examples of the alkyl group include a methyl group, ethyl group, n-propyl group, iso-propyl group, n-butyl group, n-hexyl group, n-octyl group, iso-butyl group, tert-butyl group, cyclopentyl group and cyclohexyl group. Examples of the substituted alkyl group include a fluoroalkyl group. As examples of the fluoroalkyl group, a trifluoromethyl group, pentafluoroethyl group, perfluorocyclohexyl group, perfluorooctyl group, perfluoroadamantyl group or the like can be given.

Examples of the substituted or unsubstituted aryl group include a phenyl group, biphenyl group, naphthyl group, fluorophenyl group and trifluoromethylphenyl group.

Examples of the substituted or unsubstituted heterocyclic group include pyridine, pyrazine, furan, imidazole, benzimidazole and thiophene.

As examples of the halogen atom, a fluorine atom, chlorine atom, bromine atom or iodine atom can be given.

Examples of the substituted or unsubstituted alkoxy group include a methoxy group, ethoxy group and trifluoromethoxy group.

Examples of the substituted or unsubstituted aryloxy group include a benzyloxy group, pentafluorobenzyloxy group and 4-trifluoromethylbenzyloxy group.

As examples of the substituent for the alkyl group, the aryl group, the heterocyclic group, the aryloxy group and the alkoxy group shown by $R^1$ to $R^4$ and $R^8$ to $R^{17}$, the same atoms or groups as exemplified above for the halogen atom, the cyano group, the substituted or unsubstituted alkyl group, the substituted or unsubstituted aryl group or the substituted or unsubstituted heterocyclic group can be given. Of these, fluorine, a fluoroalkyl group, a fluoroalkoxy group, a cyano group and the like are preferable.

$R^1$ and $R^2$, $R^3$ and $R^4$, and the adjacent groups of $R^8$ to $R^{11}$ and $R^{12}$ to $R^{15}$ may be bonded to each other to form a ring. Examples of the ring include a benzene ring, naphthalene ring, pyrazine ring, pyridine ring and furan ring.

It is preferred that $R^1$ to $R^4$ and $R^8$ to $R^{17}$ as mentioned above contain fluorine, a fluoroalkyl group or a fluoroalkyl-substituted aryl group in order to enhance electron acceptability, to obtain a practical sublimation temperature or to suppress crystallization.

In each of the above formulas, $X^1$ and $X^2$ are independently a divalent group shown by the following formulas (a) to (g):

(a)

(b)

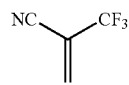
(c)

(d)

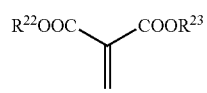
(e)

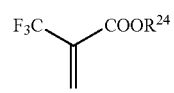
(f)

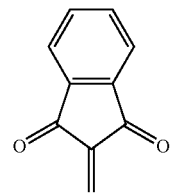
(g)

wherein $R^{21}$ to $R^{24}$, which may be the same or different, are a hydrogen atom, substituted or unsubstituted alkyl group, substituted or unsubstituted aryl group, or substituted or unsubstituted heterocyclic group; and $R^{22}$ and $R^{23}$ may be bonded to each other to form a ring.

Examples of the substituted or unsubstituted alkyl group represented by $R^{21}$ to $R^{24}$, the substituted or unsubstituted aryl group or the substituted or unsubstituted heterocyclic group shown by $R^{21}$ to $R^{24}$ are the same as those for $R^1$ or the like in the formula (I) as mentioned above. Furthermore, the examples of the ring formed by $R^{22}$ and $R^{23}$ are the same as those formed by $R^1$ and $R^2$.

In each of the above formulas, $Y^1$ and $Y^2$ are independently —N═ or —CH═ and $Y^3$ to $Y^6$ are independently —N═ or —CR═. In the formula (I), at least one of $Y^1$ to $Y^6$ is —N═. It is preferred that $Y^1$ or $Y^1$ and $Y^2$ be —N═. In the formulas (IIa) and (IIb), at least one of $Y^1$ to $Y^4$ is —N═. It is preferred that $Y^1$ and $Y^4$ or $Y^1$ to $Y^4$ be —N═.

R is the same as $R^1$ to $R^4$ as mentioned above. Preferably, R is hydrogen.

Of the compounds as exemplified above, the compounds shown by the following formula (Ib), (Ic), (IIc), (IId), (IIe) or (IIf) are preferable in respect of easiness in synthesis, heat resistance, performance of an organic EL device or the like. $R^{31}$ to $R^{48}$ are the same as $R^1$ to $R^4$ and $R^8$ to $R^{17}$ mentioned above.

The compounds shown by the formula (Ic), (IId) and (IIf) have a plurality of isomers depending on the bonding position of the cyano group of the two cyanoimine groups. The material of the invention is not restricted to a specific isomer.

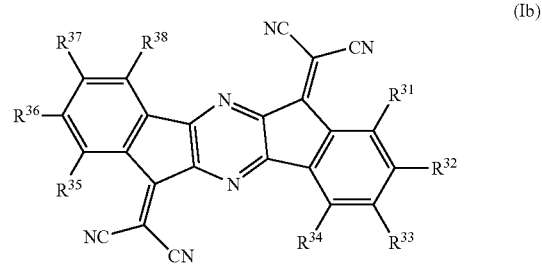
(Ib)

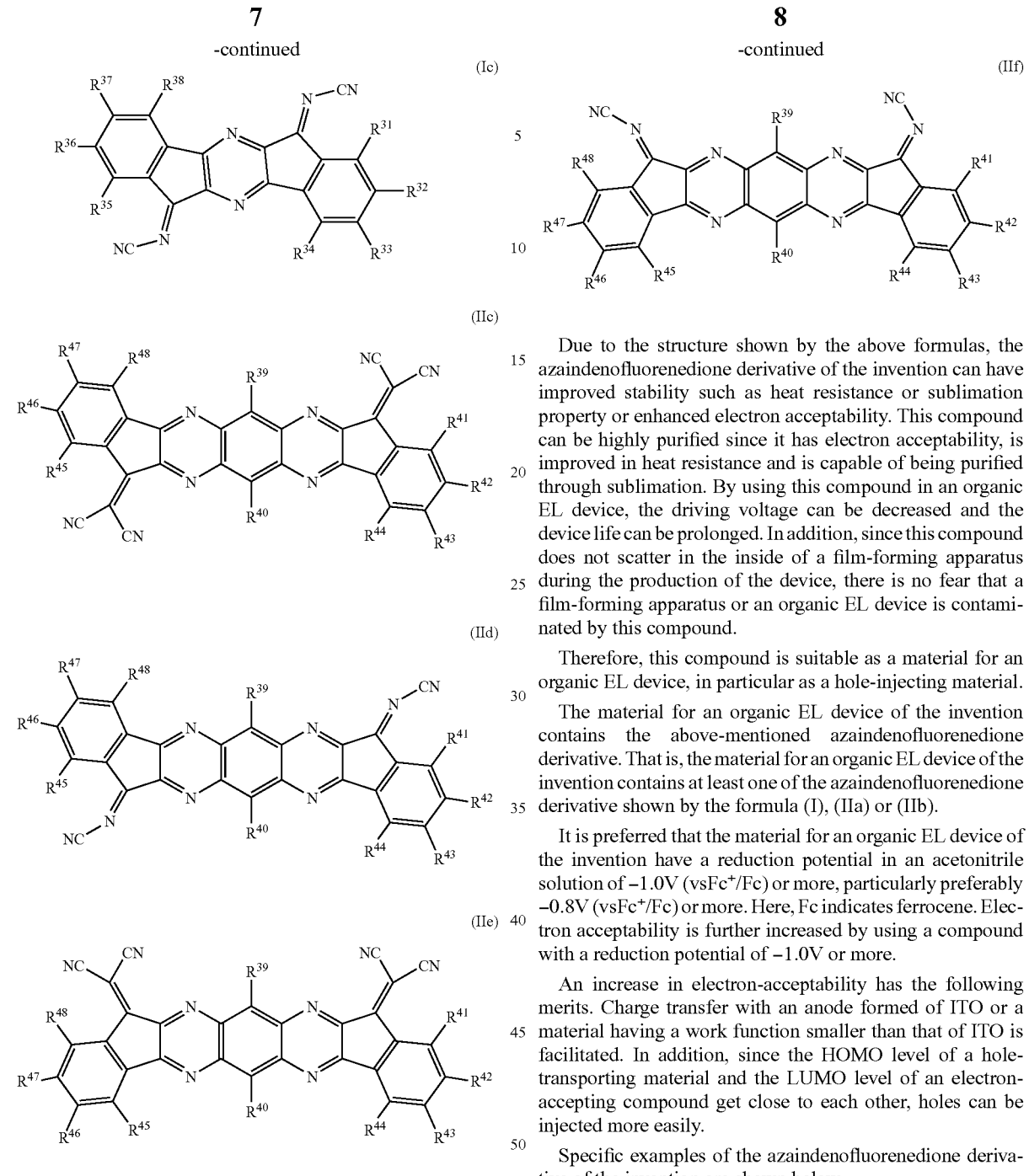

Due to the structure shown by the above formulas, the azaindenofluorenedione derivative of the invention can have improved stability such as heat resistance or sublimation property or enhanced electron acceptability. This compound can be highly purified since it has electron acceptability, is improved in heat resistance and is capable of being purified through sublimation. By using this compound in an organic EL device, the driving voltage can be decreased and the device life can be prolonged. In addition, since this compound does not scatter in the inside of a film-forming apparatus during the production of the device, there is no fear that a film-forming apparatus or an organic EL device is contaminated by this compound.

Therefore, this compound is suitable as a material for an organic EL device, in particular as a hole-injecting material.

The material for an organic EL device of the invention contains the above-mentioned azaindenofluorenedione derivative. That is, the material for an organic EL device of the invention contains at least one of the azaindenofluorenedione derivative shown by the formula (I), (IIa) or (IIb).

It is preferred that the material for an organic EL device of the invention have a reduction potential in an acetonitrile solution of −1.0V (vsFc$^+$/Fc) or more, particularly preferably −0.8V (vsFc$^+$/Fc) or more. Here, Fc indicates ferrocene. Electron acceptability is further increased by using a compound with a reduction potential of −1.0V or more.

An increase in electron-acceptability has the following merits. Charge transfer with an anode formed of ITO or a material having a work function smaller than that of ITO is facilitated. In addition, since the HOMO level of a hole-transporting material and the LUMO level of an electron-accepting compound get close to each other, holes can be injected more easily.

Specific examples of the azaindenofluorenedione derivative of the invention are shown below.

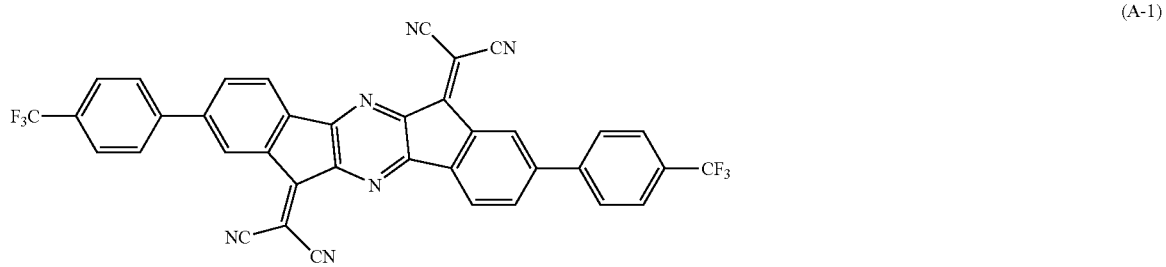

(A-1)

-continued
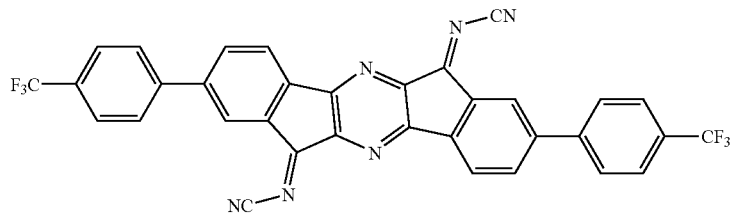
(A-2)
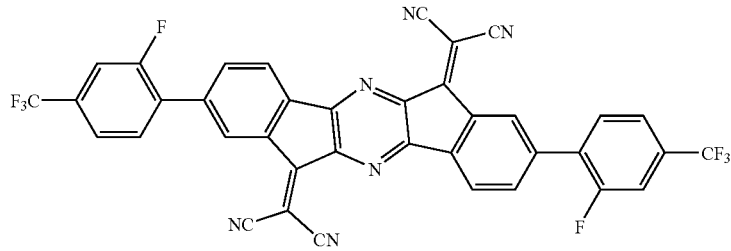
(A-3)
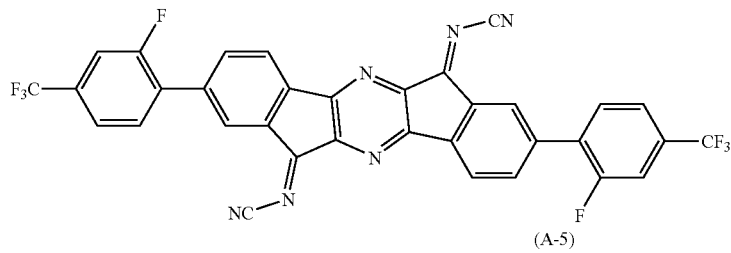
(A-4)
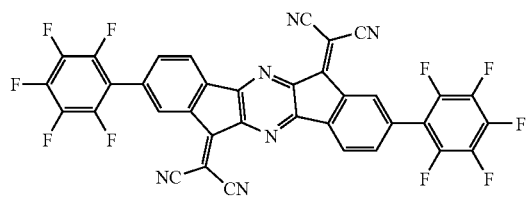
(A-5)
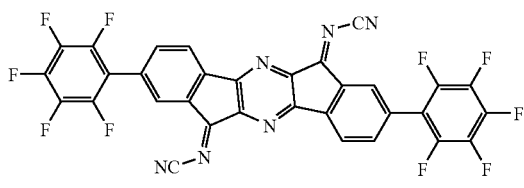
(A-6)
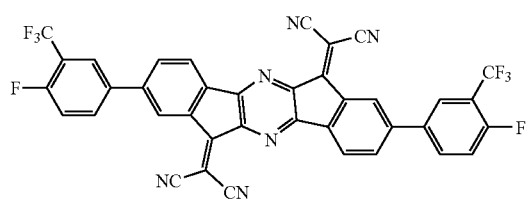
(A-7)
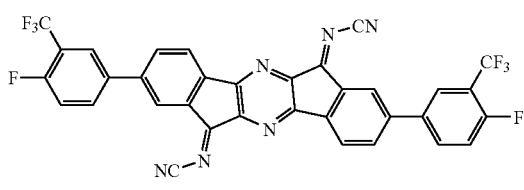
(A-8)
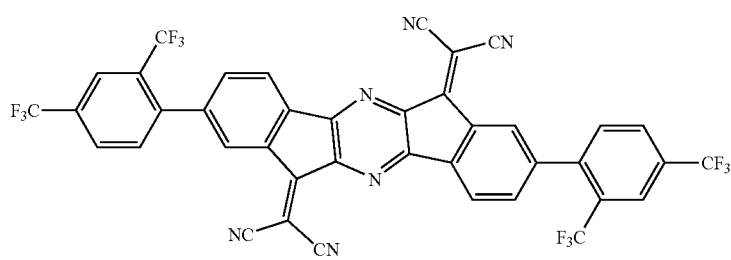
(A-9)
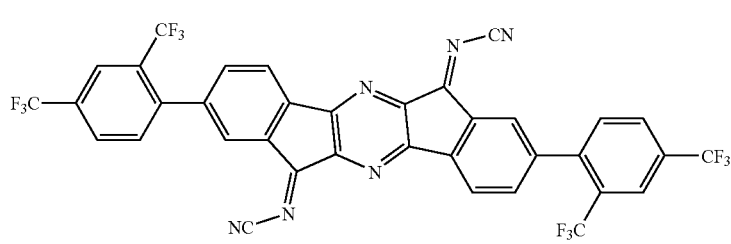
(A-10)

-continued
(A-11)
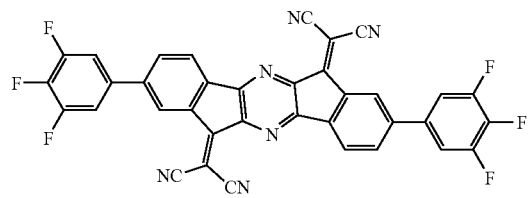
(A-12)
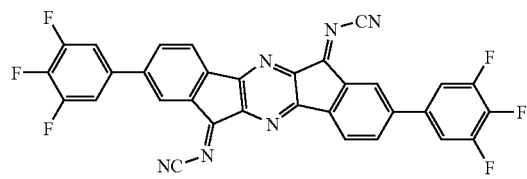
(A-13)
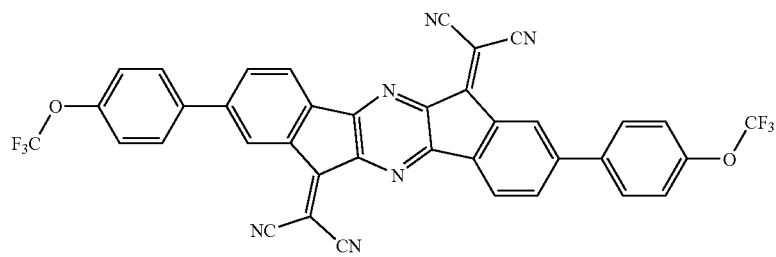
(A-14)
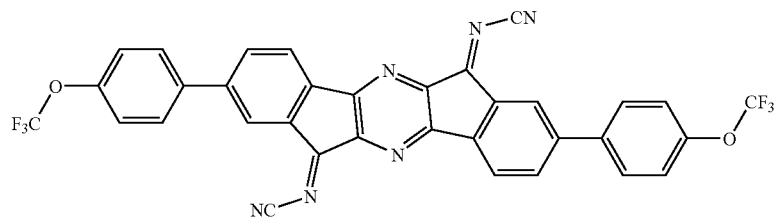
(A-15)
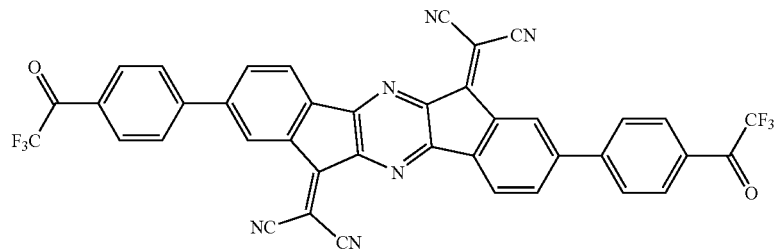
(A-16)
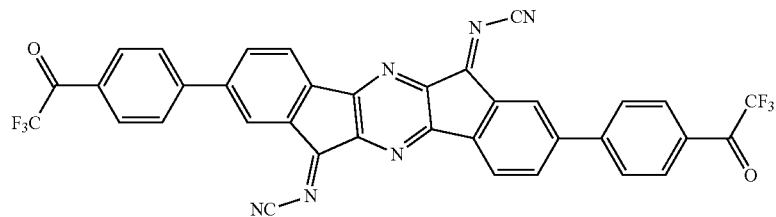
(A-17)
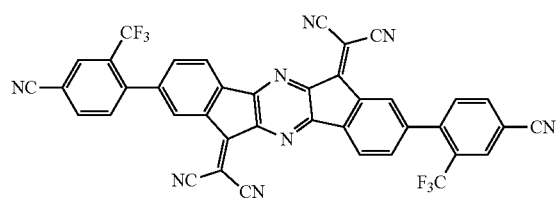
(A-18)
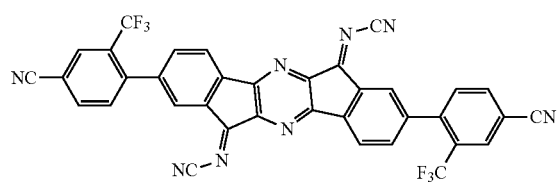

-continued
(A-19)
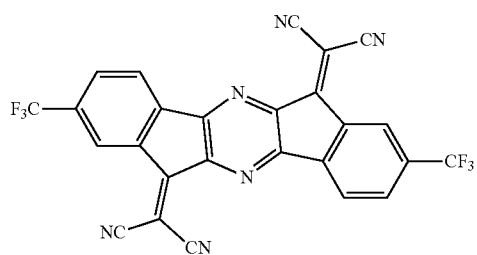
(A-20)
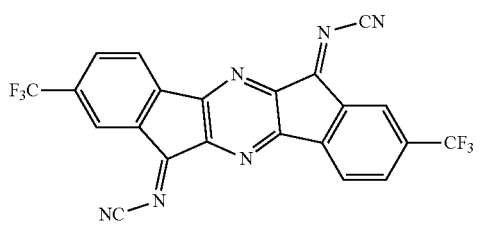
(A-21)
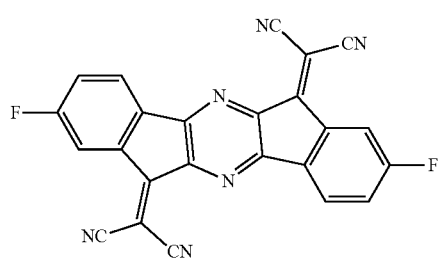
(A-22)
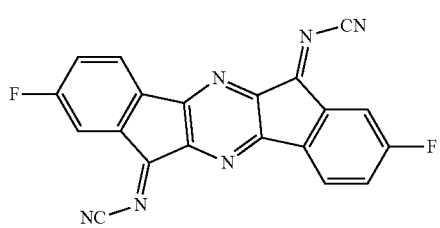
(A-23)
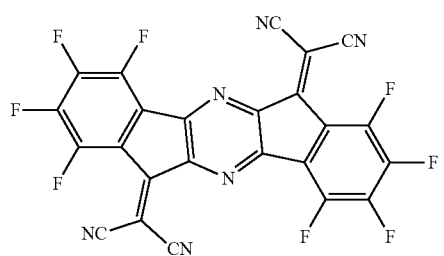
(A-24)
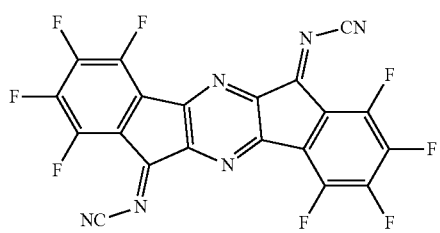
(A-25)
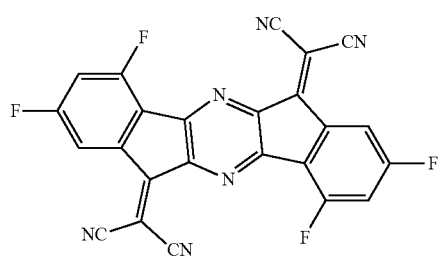
(A-26)
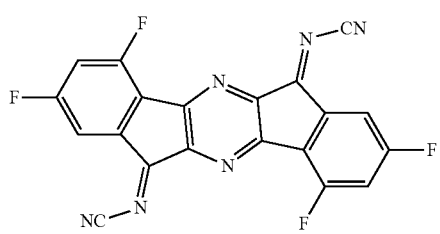
(A-27)
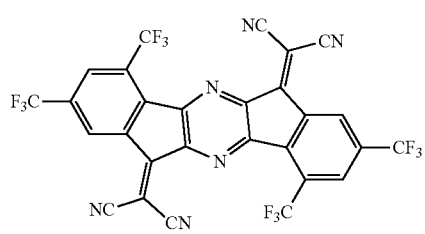
(A-28)
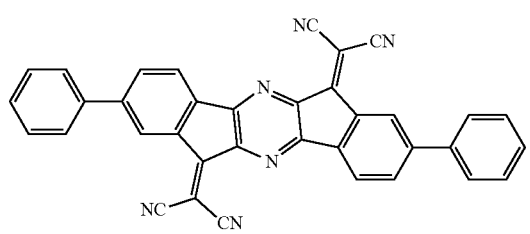

-continued
(A-29)
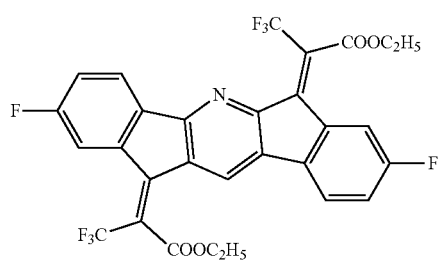
(A-30)
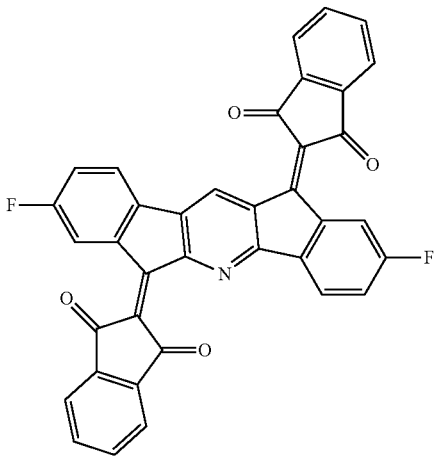
(A-31)
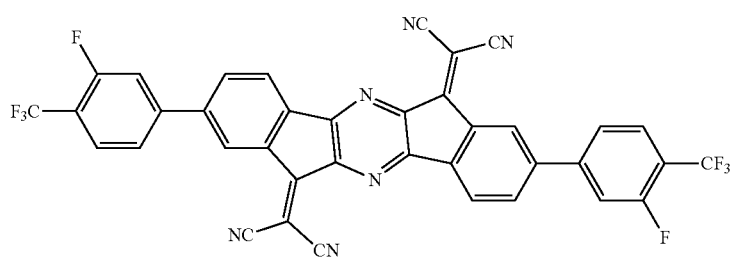
(A-32)
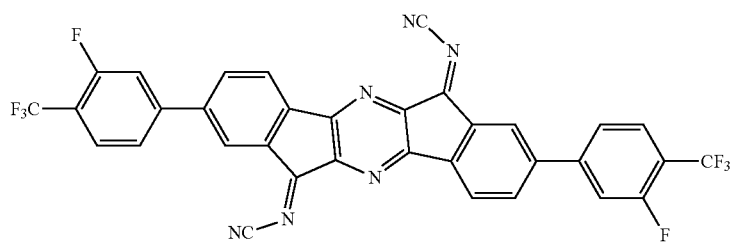
(A-33)
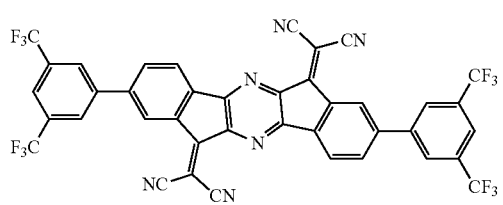
(A-34)
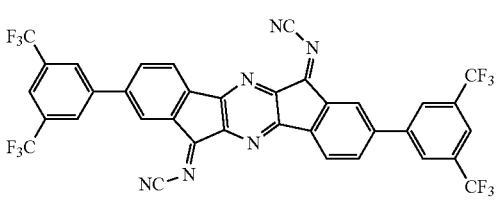
(A-35)
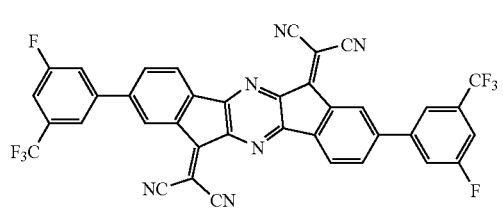
(A-36)
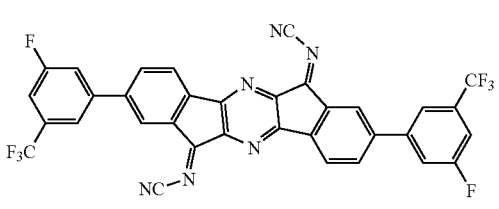
(A-37)
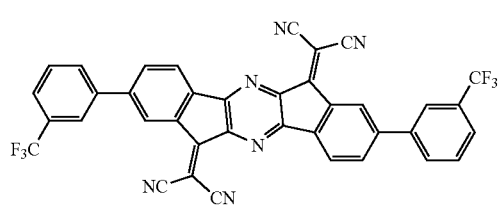
(A-38)
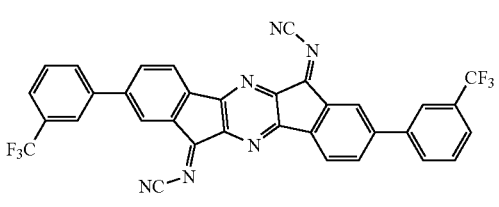

-continued
(A-39)
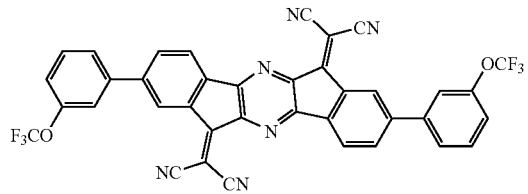
(A-40)
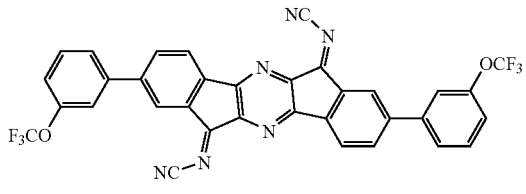
(A-41)
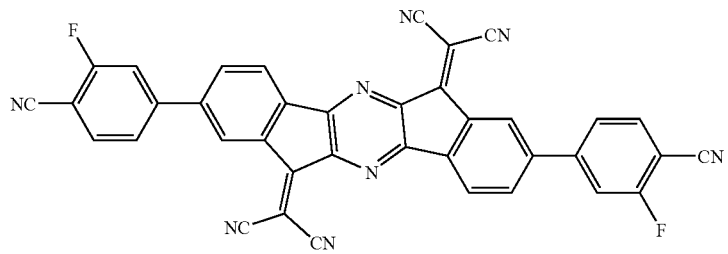
(A-42)
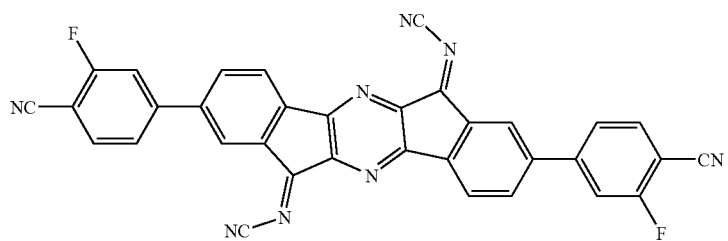
(A-43)
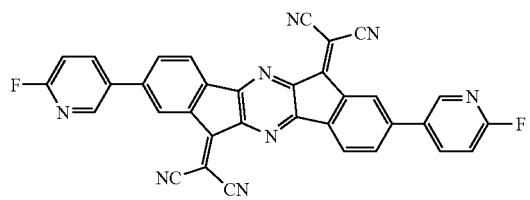
(A-44)
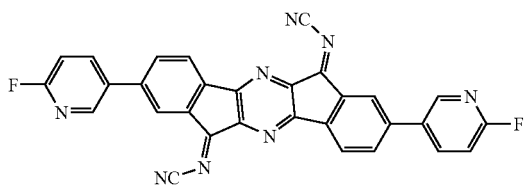
(A-45)
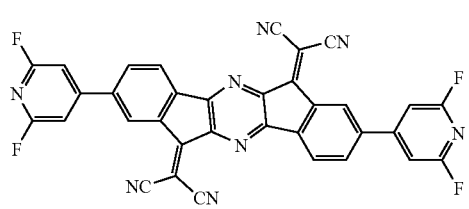
(A-46)
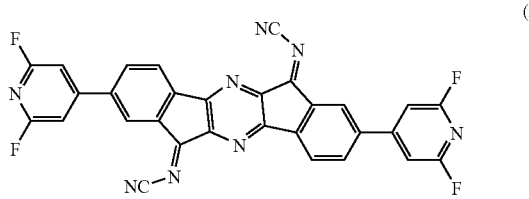
(A-47)
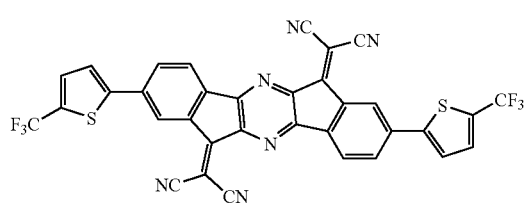
(A-48)
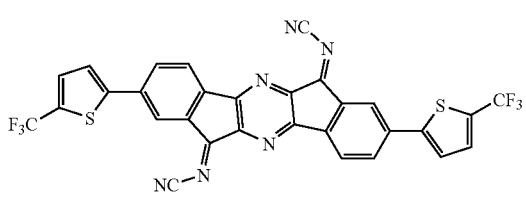
(A-49)
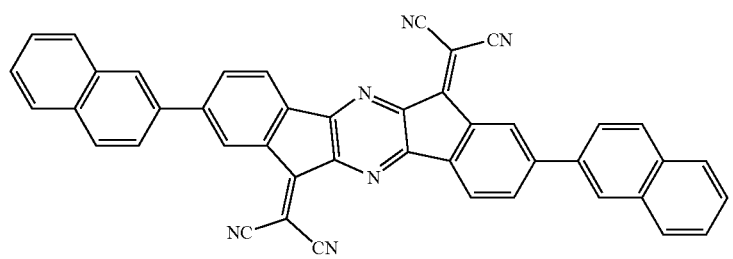

-continued
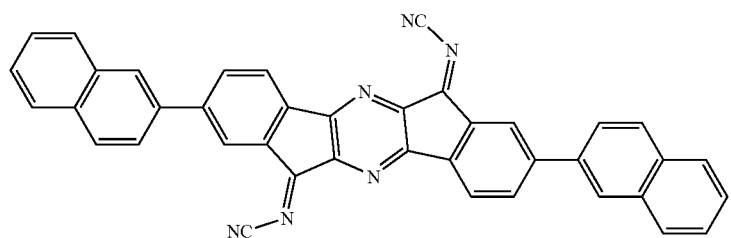
(A-50)
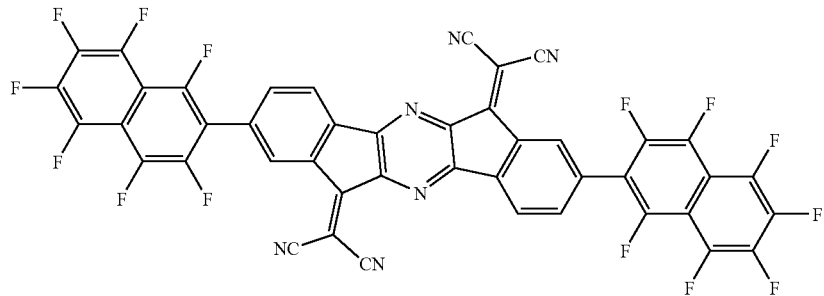
(A-51)
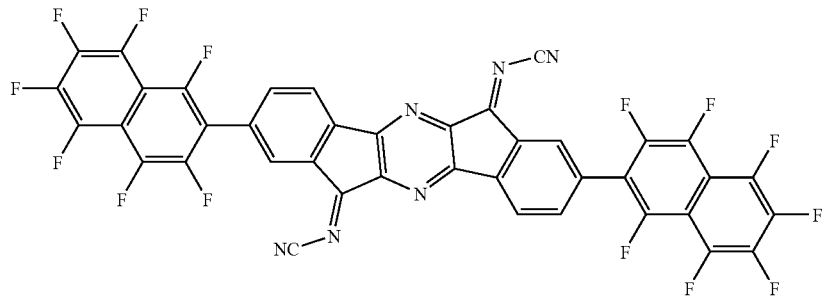
(A-52)
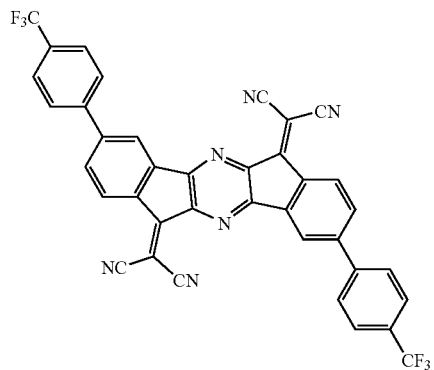
(A-53)
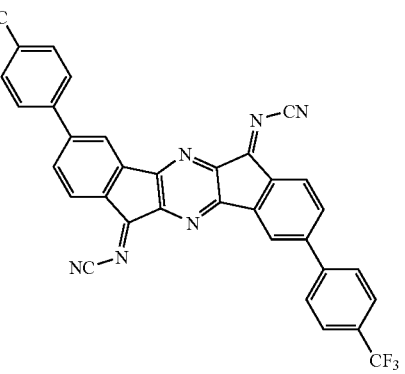
(A-54)

(A-55)
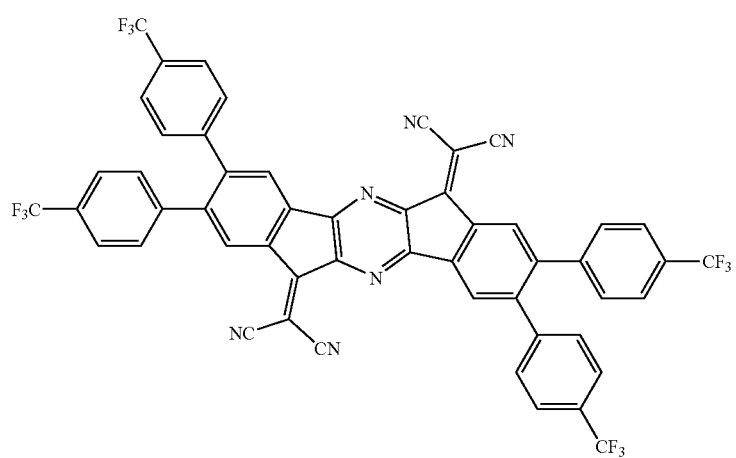
(A-56)
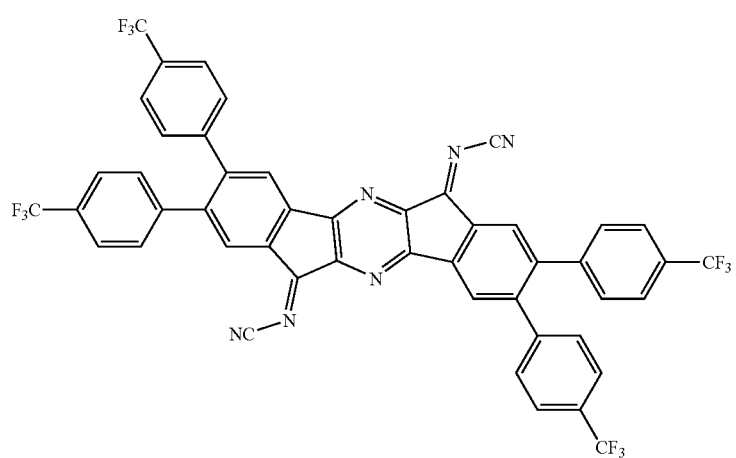
(A-57)
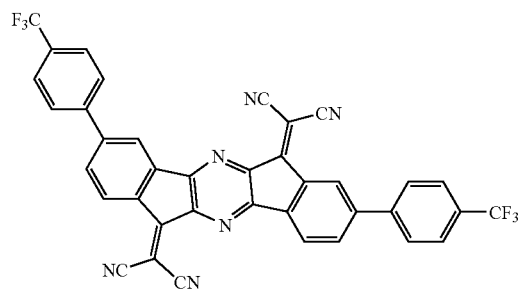
(A-58)
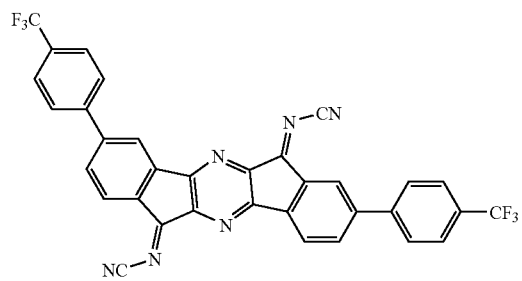
(A-59)
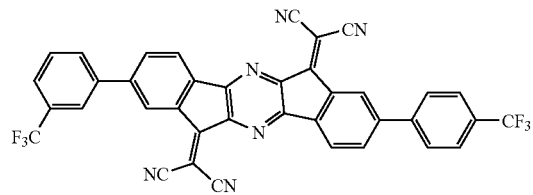
(A-60)
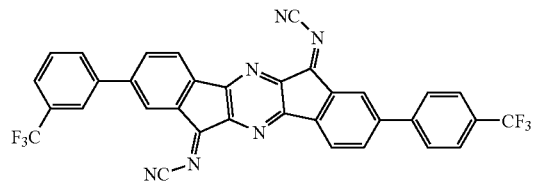

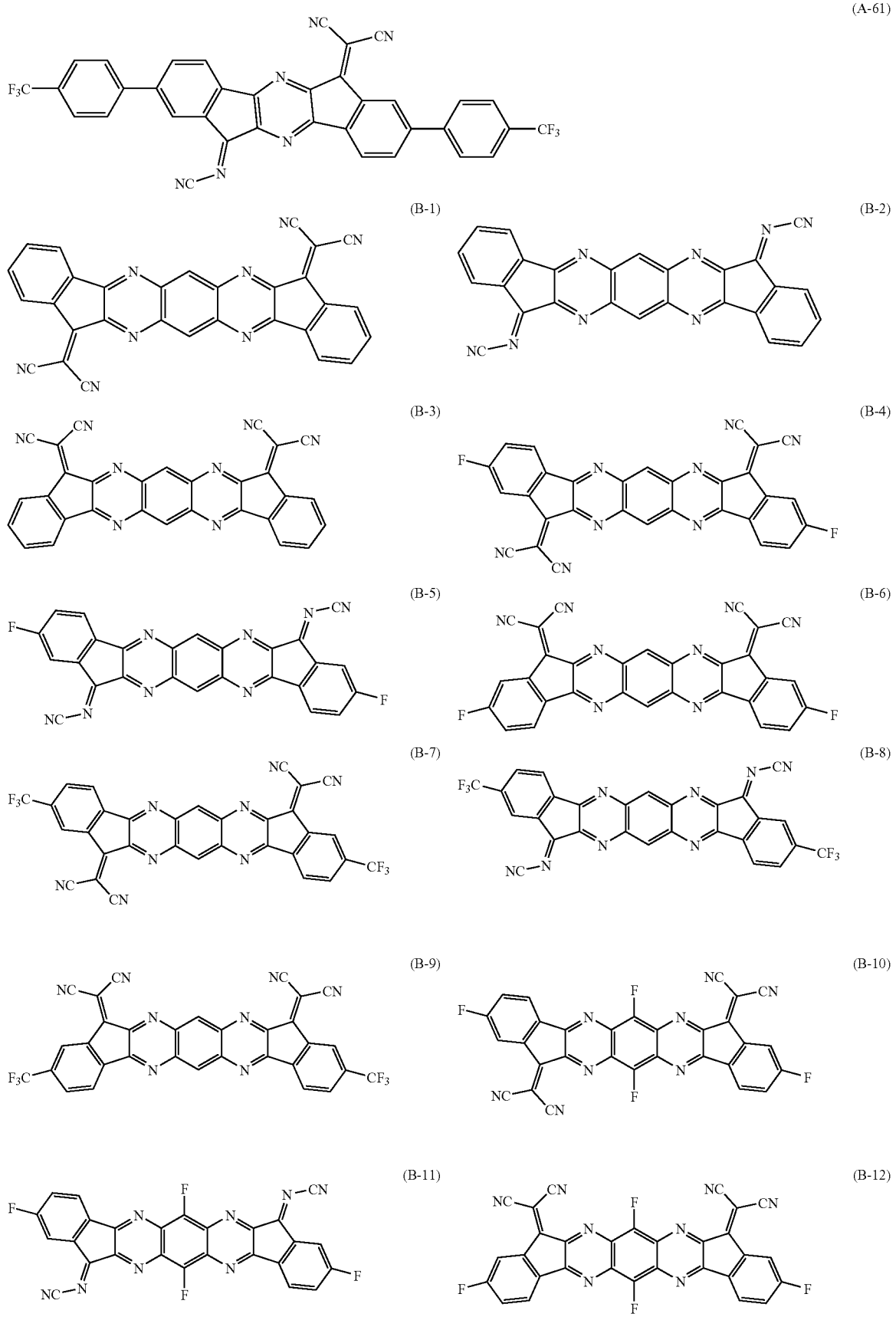

-continued
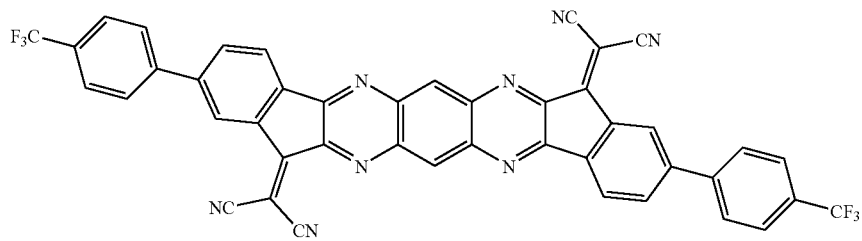
(B-13)
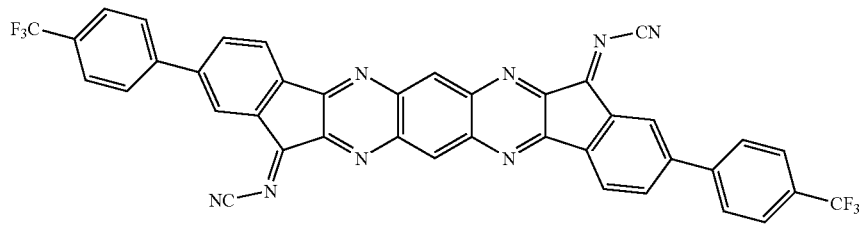
(B-14)
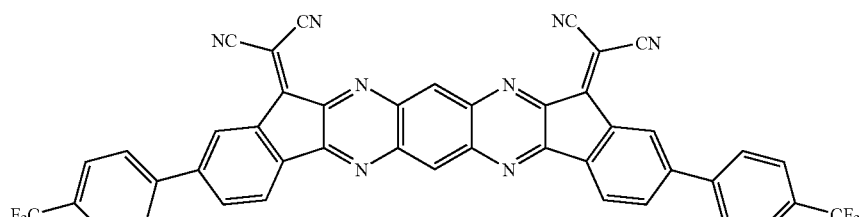
(B-15)
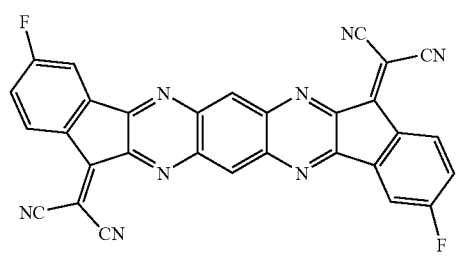
(B-16)
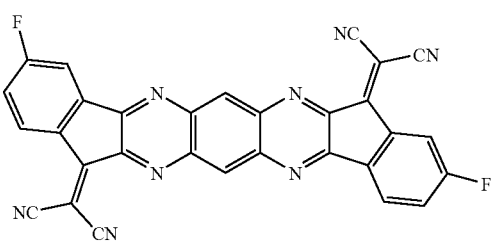
(B-17)
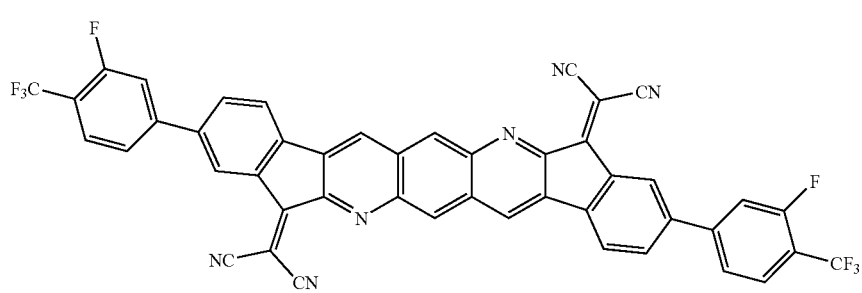
(B-18)
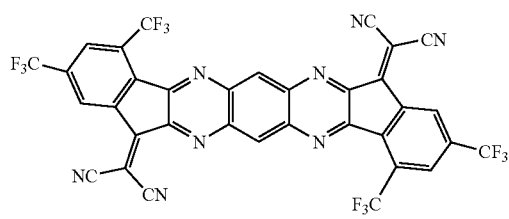
(B-19)
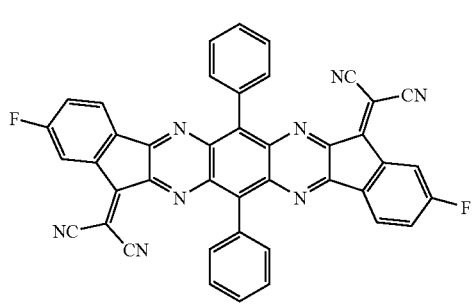
(B-20)

The azaindenofluorenedione derivative of the invention can be obtained by the following methods. For example, an azaindenofluorenedione derivative (III) is synthesized by following schemes 1 to 2 with reference to the synthesis method described in Chemische Berichte (1956), vol. 89, page 2799, Journal of Organic Chemistry (2001), vol. 66, page 7666 or the Japanese Patent No. 3098330. The azaindenofluorenedione derivative (IVa) or (IVb) is synthesized by the following scheme 3. Further, from these derivatives, by the method shown by the following scheme 4 or 5 (for the details including synthesis conditions, reference can be made of Liebigs Ann. Chem. (1986), page 142 or the like), a corresponding dicyanomethylene or cyanoimino body can be synthesized. The amount of impurities can be further decreased by subjecting the crystals obtained by these reactions to purification through sublimation, whereby the material for an organic EL device which can impart the device with excellent performance in respect of device life can be obtained.

(Scheme 1)

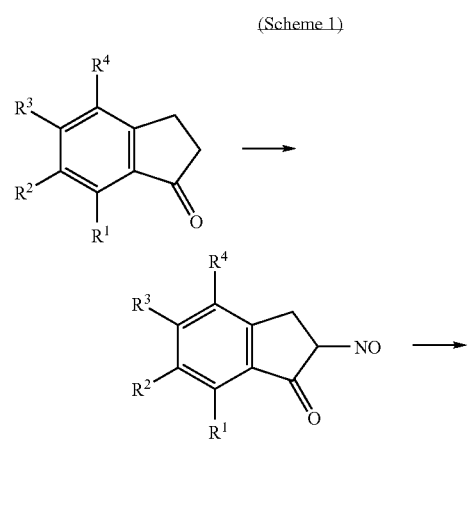

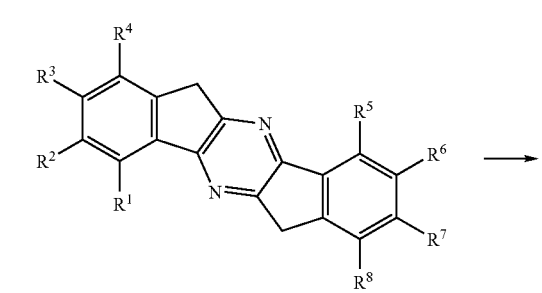

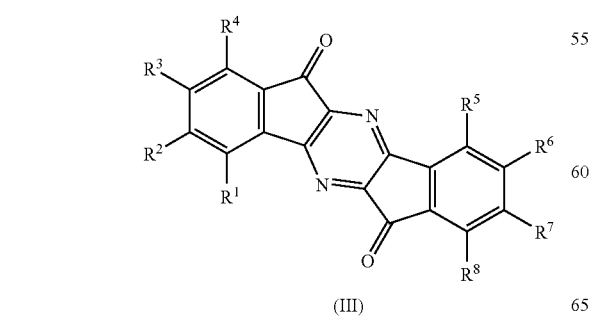

(III)

(Scheme 2)

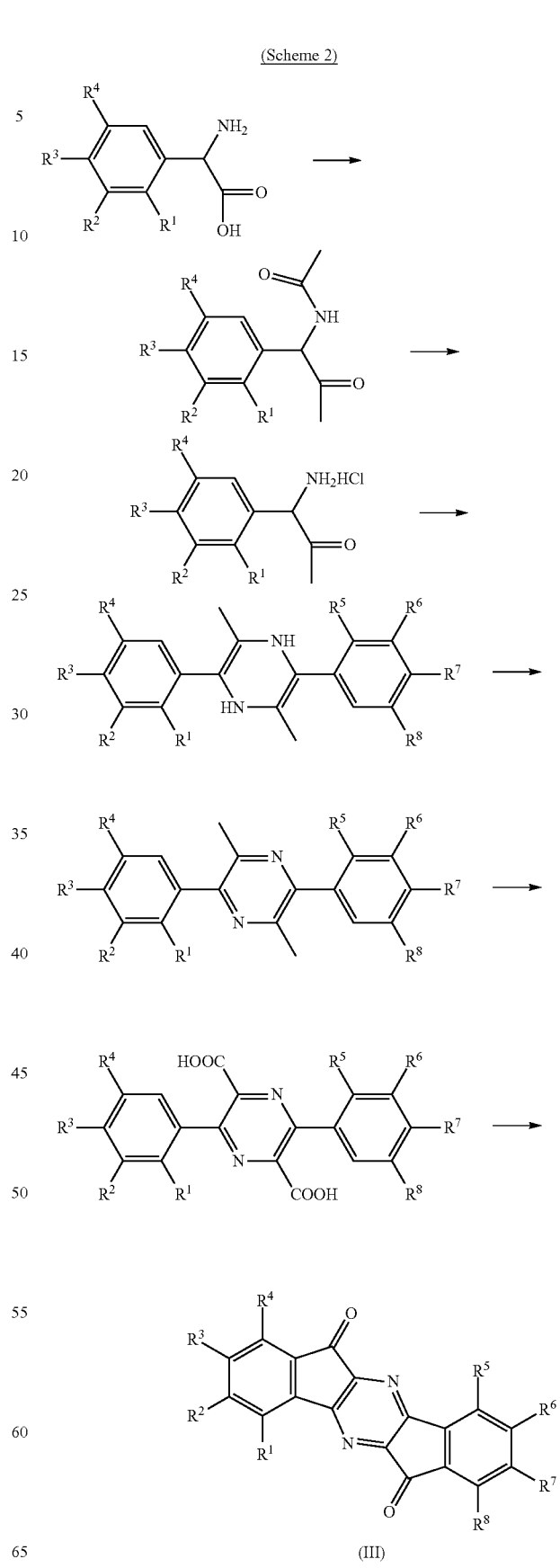

(III)

(Scheme 3)

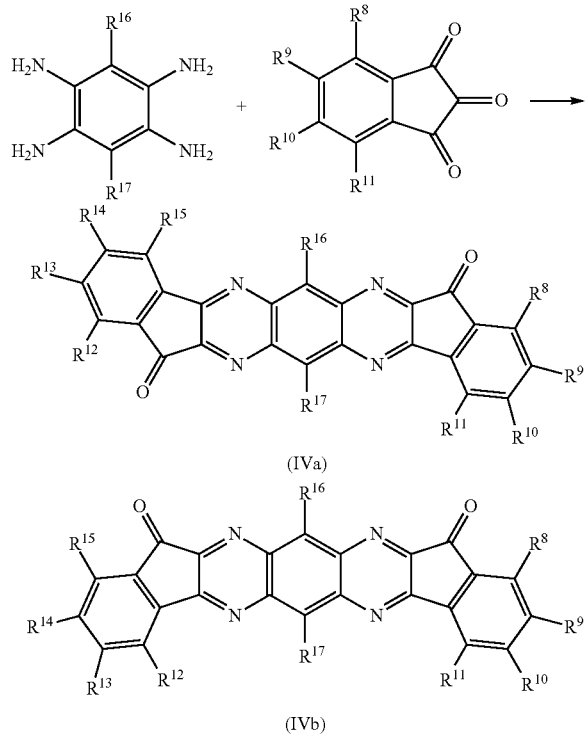

(IVa)

(IVb)

(Scheme 4)

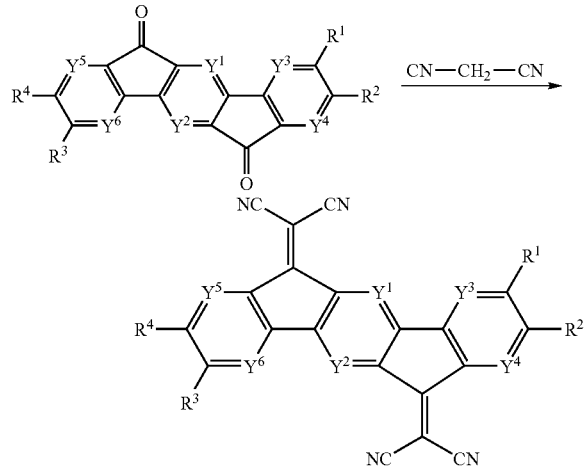

(Scheme 5)

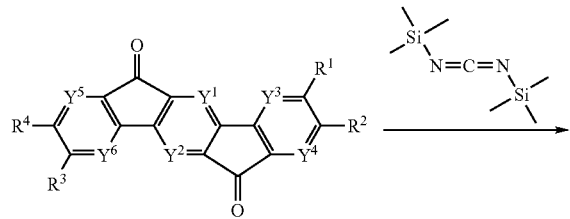

-continued

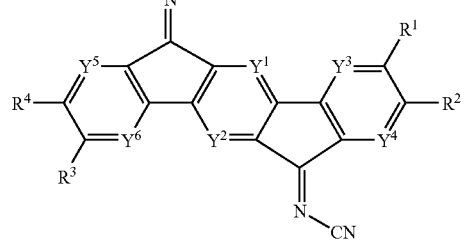

(The symbols in the structural formulas have the same meanings as in the above formula (I)).

An explanation will be made on the organic EL device of the invention.

The organic EL device of the invention has an organic thin film layer between an anode and a cathode. The organic thin film layer includes a hole-injecting layer, a hole-transporting layer, an emitting layer and an electron-transporting layer in this order, and the hole-injecting layer contains the material for an organic EL device of the invention.

FIG. 1 is a schematic cross-sectional view showing one embodiment of the organic EL device of the invention.

In an organic EL device 1, on a substrate (not shown), an anode 10, a hole-injecting layer 20, a hole-transporting layer 30, an emitting layer 40, an electron-transporting layer 50 and a cathode 60 are stacked in this order. In this device, the organic thin film layers have a multi-layer structure comprising the hole-injecting layer 20, the hole-transporting layer 30, the emitting layer 40 and the electron-transporting layer 50. In the invention, the hole-injecting layer 20 contains the material for an organic EL device of the invention. Due to this configuration, an organic EL device can be driven at a lower driving voltage and can have a long life.

Other organic layers than the hole-injecting layer may contain the material for an organic EL device of the invention. In this case, the material for an organic EL device of the invention may be used in a mixture with material constituting each layer which will be mentioned later.

The content of the material for an organic EL device of the invention in the hole-injecting layer is preferably 1 to 100 mol %.

The material for an organic EL device of the invention can be applied to devices having other configuration than that in the above embodiment. For example, in devices with the configurations (1) to (15) shown below, the material for an organic EL device of the invention may be used as the material of each organic layer such as an emitting layer constituting the device.

(1) Anode/emitting layer/cathode
(2) Anode/hole-transporting layer/emitting layer/cathode
(3) Anode/emitting layer/electron-transporting layer/cathode
(4) Anode/hole-transporting layer/emitting layer/electron-transporting layer/cathode
(5) Anode/hole-transporting layer/emitting layer/adhesion-improving layer/cathode
(6) Anode/hole-injecting layer/hole-transporting layer/emitting layer/electron-transporting layer/cathode (FIG. 1)
(7) Anode/hole-transporting layer/emitting layer/electron-transporting layer/electron-injecting layer/cathode
(8) Anode/hole-injecting layer/hole-transporting layer/emitting layer/electron-transporting layer/electron-injecting layer/cathode
(9) Anode/insulating layer/hole-transporting layer/emitting layer/electron-transporting layer/cathode

(10) Anode/hole-transporting layer/emitting layer/electron-transporting layer/insulating layer/cathode

(11) Anode/inorganic semiconductor layer/insulating layer/hole-transporting layer/emitting layer/insulating layer/cathode

(12) Anode/insulating layer/hole-transporting layer/emitting layer/electron-transporting layer/insulating layer/cathode

(13) Anode/hole-injecting layer/hole-transporting layer/emitting layer/electron-transporting layer/insulating layer/cathode

(14) Anode/insulating layer/hole-injecting layer/hole-transporting layer/emitting layer/electron-transporting layer/electron-injecting layer/cathode

(15) Anode/insulating layer/hole-injecting layer/hole-transporting layer/emitting layer/electron-transporting layer/electron-injecting layer/insulating layer/cathode Among these, usually, the structures (4), (6), (7), (8), (12), (13) and (15) are preferably used.

Each member constituting the organic EL device of the invention will be described below.

(Transparent Substrate)

The organic EL device is usually formed on a transparent substrate. The transparent substrate is a substrate for supporting the organic EL device, and is preferably a flat and smooth substrate having a 400-to-700-nm-visible-light transmittance of 50% or more.

Specific examples thereof include glass plates and polymer plates. Examples of the glass plate include soda-lime glass, barium/strontium-containing glass, lead glass, aluminosilicate glass, borosilicate glass, barium borosilicate glass, and quartz. Examples of the polymer plate include polycarbonate, acrylic polymer, polyethylene terephthalate, polyethersulfone, and polysulfone.

Transparency is not required when the supporting substrate is positioned in the direction opposite to the light-outcoupling direction.

(Anode)

The anode of the organic EL device plays a role for injecting holes into its hole-transporting layer or emitting layer. When transparency is required for the anode, indium tin oxide alloy (ITO), tin oxide (NESA), indium zinc-oxide alloy, gold, silver, platinum, copper, and the like may be used as the material for the anode. When a reflective electrode which does not require transparency is used, a metal such as aluminum, molybdenum, chromium, and nickel or alloys thereof may also be used.

In particular, an anode having a small work function (for example, 5.0 eV or less) and a hole-injecting layer using the material for an organic EL device of the invention are used in combination, charge transfer is possible, and excellent injection properties are exhibited.

Although these materials may be used singly, alloys thereof or materials wherein another element is added to the materials can be appropriately selected for use.

The anode can be formed by forming these electrode materials into a thin film by vapor deposition, sputtering or the like.

In the case where emission from the emitting layer is outcoupled through the anode, the transmittance of the anode to the emission is preferably more than 10%. The sheet resistance of the anode is preferably several hundred Ω/☐ or less. The film thickness of the anode, which varies depending upon the material thereof, is usually from 10 nm to 1 µm, preferably from 10 to 200 nm.

(Emitting Layer)

The emitting layer of the organic EL device has the following functions (1), (2) and (3) in combination.

(1) Injection function: function of allowing injection of holes from the anode or hole-injecting layer and injection of electrons from the cathode or electron-injecting layer upon application of an electric field (2) Transporting function: function of moving injected carriers (electrons and holes) due to the force of an electric field (3) Emitting function: function of allowing electrons and holes to recombine therein to emit light Note that electrons and holes may be injected into the emitting layer with different degrees, or the transportation capabilities indicated by the mobility of holes and electrons may differ. It is preferable that the emitting layer move either electrons or holes.

As the method of forming the emitting layer, a known method such as deposition, spin coating, or an LB method may be applied. It is preferable that the emitting layer be a molecular deposition film. Here, the molecular deposition film means a thin film formed by deposition of a material compound in a vapor phase or a film formed by solidification of a material compound which is in a solution state or in a liquid state. The molecular deposition film is usually distinguished from a thin film (molecular deposition film) formed using the LB method by the difference in aggregation structure or higher order structure or the difference in function due to the difference in structure.

The emitting layer may also be formed by dissolving a binder such as a resin and a material compound in a solvent to obtain a solution, and forming a thin film from the solution by spin coating or the like.

In the invention, if need arises, known emitting materials other than the compound of the invention may be contained in the emitting layer insofar as the object of the invention is not impaired. An emitting layer containing other known emitting materials may be stacked on the emitting layer containing the compound of the invention.

As the emitting material which can be used in the emitting layer, anthracene, naphthalene, phenanthrene, pyrene, tetracene, coronene, chrysene, fluorescein, perylene, phthaloperylene, naphthaloperylene, perynone, phthaloperynone, naphthaloperynone, diphenylbutadiene, tetraphenylbutadiene, coumarin, oxadiazole, aldazine, bisbenzoxazoline, bisstyryl, pyrazine, cyclopentadiene, a quinoline metal complex, an aminoquinoline metal complex, a benzoquinoline metal complex, imine, diphenylethylene, vinylanthracene, diaminocarbazole, pyran, thiopyran, polymethine, merocyanine, an imidazole chelate oxanoid compound, quinacridone, rubrene, a fluorescent pigment and like can be given. Note that the emitting materials are not limited to these compounds.

As the host material for use in the emitting layer, the compounds shown by the following formulas (i) to (ix) can be given.

Asymmetrical anthracene shown by the following formula (i):

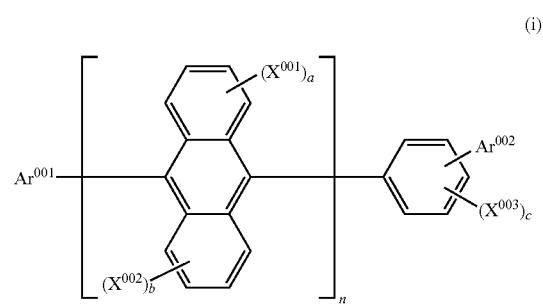

wherein $Ar^{001}$ is a substituted or unsubstituted condensed aromatic group having 10 to 50 carbon atoms that form an aromatic ring (hereinafter referred to as "ring carbon atoms"), $Ar^{002}$ is a substituted or unsubstituted aromatic group having 6 to 50 ring carbon atoms, and $X^{001}$ to $X^{003}$ are independently a substituted or unsubstituted aromatic group having 6 to 50 ring carbon atoms, a substituted or unsubstituted aromatic heterocyclic group having 5 to 50 atoms that form a ring (hereinafter referred to as "ring atoms"), a substituted or unsubstituted alkyl group having 1 to 50 carbon atoms, a substituted or unsubstituted alkoxy group having 1 to 50 carbon atoms, a substituted or unsubstituted aralkyl group having 6 to 50 carbon atoms, a substituted or unsubstituted aryloxy group having 5 to 50 ring atoms, a substituted or unsubstituted arylthio group having 5 to 50 ring atoms, a substituted or unsubstituted alkoxycarbonyl group having 1 to 50 carbon atoms, a carboxyl group, a halogen atom, a cyano group, a nitro group or a hydroxyl group. a, b and c are each an integer of 0 to 4. n is an integer of 1 to 3. When n is 2 or more, the group in [ ] may be the same or different.

Asymmetrical monoanthracene derivatives shown by the following formula (ii):

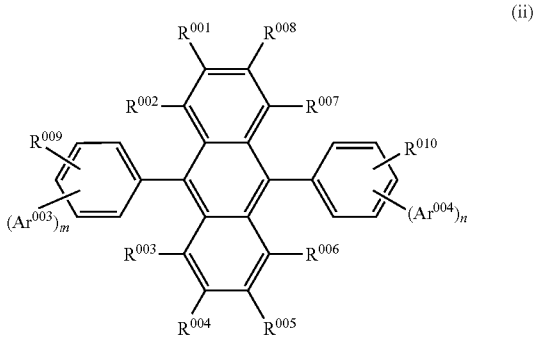

wherein $Ar^{003}$ and $Ar^{004}$ are independently a substituted or unsubstituted aromatic ring group having 6 to 50 ring carbon atoms, and m and n are each an integer of 1 to 4, provided that in the case where m=n=1 and $Ar^{003}$ and $Ar^{004}$ are symmetrically bonded to the benzene rings, $Ar^{003}$ and $Ar^{004}$ are not the same, and in the case where morn is an integer of 2 to 4, m is different from n.

$R^{001}$ to $R^{010}$ are independently a hydrogen atom, a substituted or unsubstituted aromatic ring group having 6 to 50 ring carbon atoms, a substituted or unsubstituted aromatic hetrocyclic group having 5 to 50 ring atoms, a substituted or unsubstituted alkyl group having 1 to 50 carbon atoms, a substituted or unsubstituted cycloalkyl group, a substituted or unsubstituted alkoxy group having 1 to 50 carbon atoms, a substituted or unsubstituted aralkyl group having 6 to 50 carbon atoms, a substituted or unsubstituted aryloxy group having 5 to 50 ring atoms, a substituted or unsubstituted arylthio group having 5 to 50 ring atoms, a substituted or unsubstituted alkoxycarbonyl group having 1 to 50 carbon atoms, a substituted or unsubstituted silyl group, a carboxyl group, a halogen atom, a cyano group, a nitro group or a hydroxyl group.

Asymmetrical pyrene derivatives shown by the following formula (iii):

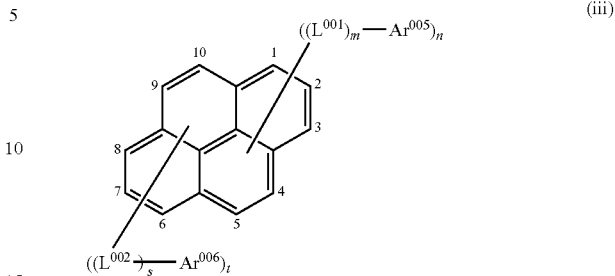

wherein $Ar^{005}$ and $Ar^{006}$ are independently a substituted or unsubstituted aromatic group having 6 to 50 ring carbon atoms; $L^{001}$ and $L^{002}$ are each a substituted or unsubstituted phenylene group, a substituted or unsubstituted naphthalenylene group, a substituted or unsubstituted fluolenylene group, or a substituted or unsubstituted dibenzosilolylene group;

m is an integer of 0 to 2, n is an integer of 1 to 4, s is an integer of 0 to 2, and t is an integer of 0 to 4; and $L^{001}$ or $Ar^{005}$ bonds at any one position of 1 to 5 of the pyrene, and $L^{002}$ or $Ar^{006}$ bonds at any one position of 6 to 10 of the pyrene; provided that when n+t is an even number, $Ar^{005}$, $Ar^{006}$, $L^{001}$ and $L^{002}$ satisfy the following (1) or (2):

(1) $Ar^{005} \ne Ar^{006}$ and/or $L^{001} \ne L^{002}$ where ≠ means these substituents are groups having different structures from each other, (2) When $Ar^{005}=Ar^{006}$ and $L^{001}=L^{002}$ (2-1) m≠s and/or n≠t, or (2-2) when m=s and n=t, (2-2-1) when $L^{001}$ and $L^{002}$ or pyrene are independently bonded to different bonding positions of $Ar^{005}$ and $Ar^{006}$, or (2-2-2) when $L^{001}$ and $L^{002}$ or pyrene are bonded to the same position of $Ar^{005}$ and $Ar^{006}$, the positions of the substitution of $L^{001}$ and $L^{002}$ or $Ar^{005}$ and $Ar^{006}$ at pyrene are neither the 1$^{st}$ position and the 6$^{th}$ position, nor the 2$^{nd}$ position and the 7$^{th}$ position.

Asymmetrical anthracene derivatives shown by the following formula (iv):

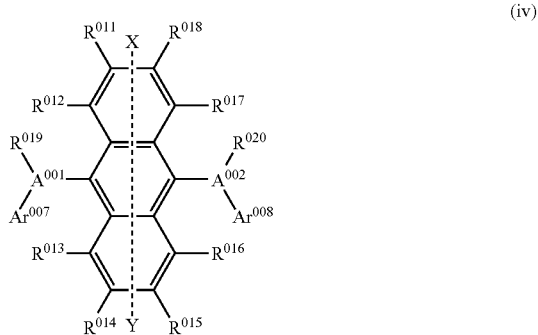

wherein $A^{001}$ and $A^{002}$ are independently a substituted or unsubstituted condensed aromatic ring group having 10 to 20 ring carbon atoms, $Ar^{007}$ and $Ar^{008}$ are independently a hydrogen atom or a substituted or unsubstituted aromatic ring group with 6 to 50 ring carbon atoms, $R^{011}$ to $R^{020}$ are independently a hydrogen atom, a substituted or unsubstituted aromatic ring group having 6 to 50 ring carbon atoms, a substituted or unsubstituted aromatic heterocyclic group having 5 to 50 ring atoms, a substituted or unsubstituted alkyl group having 1 to 50 carbon atoms, a substituted or unsubstituted cycloalkyl group, a substituted or unsubstituted alkoxy group having 1 to 50 carbon atoms, a substituted or unsubstituted aralkyl group having 6 to 50 carbon atoms, a substituted or unsubstituted aryloxy group having 5 to 50 ring atoms, a substituted or unsubstituted arylthio group having 5 to 50 ring atoms, a substituted or unsubstituted alkoxycarbonyl group having 1 to 50 carbon atoms, a substituted or unsubstituted silyl group, a carboxyl group, a halogen atom, a cyano group, a nitro group or a hydroxyl group, and each of $Ar^{007}$, $Ar^{008}$, $R^{019}$ and $R^{020}$ may be plural, and adjacent groups thereof may form a saturated or unsaturated ring structure, provided that groups do not symmetrically bond to the $9^{th}$ and $10^{th}$ positions of the central anthracene with respect to X-Y axis.

Anthracene derivatives shown by the following formula (v):

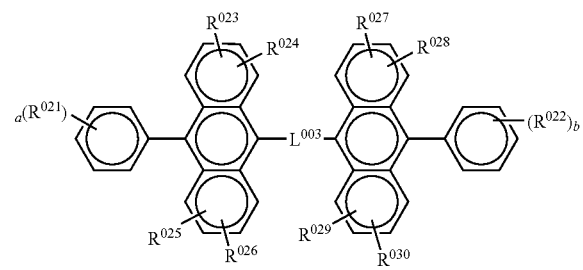

(v)

wherein $R^{021}$ to $R^{030}$ are independently a hydrogen atom, an alkyl group, a cycloalkyl group, an aryl group which may be substituted, an alkoxy group, an aryloxy group, an alkylamino group, an alkenyl group, an arylamino group or a heterocyclic group which may be substituted; a and b are each an integer of 1 to 5; when they are 2 or more, $R^{021}$s or $R^{022}$s may be the same or different, or $R^{021}$s or $R^{022}$s may be bonded to each other to form a ring; $R^{023}$ and $R^{024}$, $R^{025}$ and $R^{026}$, $R^{027}$ and $R^{028}$, or $R^{029}$ and $R^{030}$ may be bonded to each other to form a ring; and $L^{003}$ is a single bond, —O—, —S—, —N(R)— (R is an alkyl group or a substituted or unsubstituted aryl group), an alkylene group or an arylene group.

Anthracene derivatives shown by the following formula (vi):

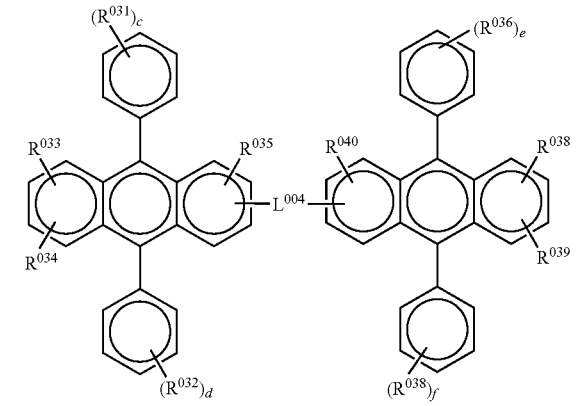

(vi)

wherein $R^{031}$ to $R^{040}$ are independently a hydrogen atom, an alkyl group, a cycloalkyl group, an aryl group, an alkoxy group, an aryloxy group, an alkylamino group, an arylamino group or a heterocyclic group which may be substituted; c, d, e and f are each an integer of 1 to 5; when they are 2 or more, $R^{031}$s, $R^{032}$s, $R^{036}$s or $R^{037}$s may be the same or different, $R^{031}$s, $R^{032}$s, $R^{033}$s or $R^{037}$s may be bonded to each other to form a ring, or $R^{033}$ and $R^{034}$, or $R^{039}$ and $R^{040}$ may be bonded to each other to form a ring; and $L^{004}$ is a single bond, —O—, —S—, —N(R)— (R is an alkyl group or a substituted or unsubstituted aryl group), an alkylene group or an arylene group.

Spirofluorene derivatives shown by the following formula (vii):

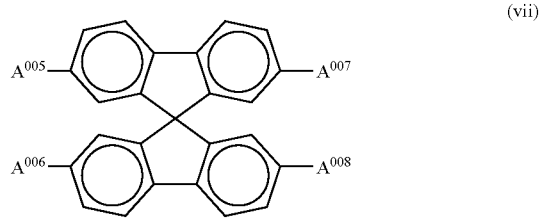

(vii)

wherein $A^{005}$ to $A^{008}$ are independently a substituted or unsubstituted biphenyl group or a substituted or unsubstituted naphthyl group.

Condensed ring-containing compounds shown by the following formula (viii):

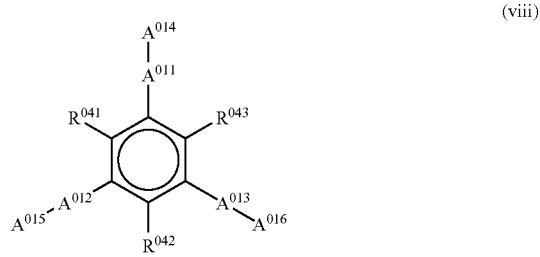

(viii)

wherein $A^{011}$ to $A^{013}$ are independently a substituted or unsubstituted arylene group having 6 to 50 ring carbon atoms; $A^{014}$ to $A^{016}$ are independently a hydrogen atom, or a substituted or unsubstituted aryl group having 6 to 50 ring carbon atoms; and $R^{041}$ to $R^{043}$ are independently a hydrogen atom, an alkyl group having 1 to 6 carbon atoms, a cycloalkyl group having 3 to 6 carbon atoms, an alkoxyl group having 1 to 6 carbon atoms, an aryloxy group having 5 to 18 carbon atoms, an aralkyloxy group having 7 to 18 carbon atoms, an arylamino group having 5 to 16 carbon atoms, a nitro group, a cyano group, an ester group having 1 to 6 carbon atoms or a halogen atom, provided that at least one of $A^{011}$ to $A^{016}$ is a group having a condensed aromatic ring with three or more rings.

Fluorene compounds shown by the following formula (ix):

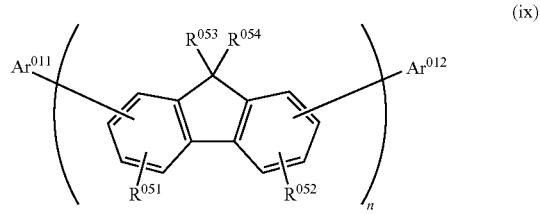

(ix)

wherein $R^{051}$ and $R^{052}$ are a hydrogen atom, a substituted or unsubstituted alkyl group, substituted or unsubstituted aralkyl group, substituted or unsubstituted aryl group, substituted or unsubstituted heterocyclic group, substituted amino group, cyano group, or a halogen atom; $R^{051}$s and $R^{052}$s bonded to different fluorene groups may be the same or different, and $R^{051}$ and $R^{052}$ bonded to a single fluorene group may be the same or different; $R^{053}$ and $R^{054}$ are a hydrogen atom, a substituted or unsubstituted alkyl group, substituted or unsubstituted aralkyl group, substituted or unsubstituted aryl group, or substituted or unsubstituted heterocyclic group, provided that $R^{053}$s or $R^{054}$s bonded to different fluorene groups may be the same or different, and $R^{053}$ and $R^{054}$ bonded to a single fluorene group may be the same or different; $Ar^{011}$ and $Ar^{012}$ are a substituted or unsubstituted condensed polycyclic aromatic group with a total number of benzene rings of three or more or a substituted or unsubstituted condensed polycyclic heterocyclic group which is bonded to the fluorene group through carbon and has a total number of benzene rings and heterocyclic rings of three or more, provided that $Ar^{011}$ and $Ar^{012}$ may be the same or different; and n is an integer of 1 to 10.

Among the above-mentioned host materials, the anthracene derivative is preferable, and the monoanthracene derivative is more preferable with the asymmetrical anthracene being particularly preferable.

Phosphorescent compounds can be used as an emitting material. When using a phosphorescent compound, compounds containing a carbazole ring are preferred for a host material. A dopant is a compound that can emit light from triplet excitons. The dopant is not particularly limited so long as it can emit light from triplet excitons, but it is preferably a metal complex containing at least one metal selected from the group of Ir, Ru, Pd, Pt, Os and Re. A porphyrin metal complex or an ortho-metalated metal complex is preferable.

The compound containing a carbazole ring, which is a host suitable for phosphorescence emission, is a compound which allows a phosphorescent compound to emit as a result of energy transfer from its excited state to the phosphorescent compound. The host compound is not particularly limited so long as the compound can transfer its excited energy to a phosphorescent compound and it can be selected depending on purposes. The host compound may contain any heterocyclic ring other than a carbazole ring.

Specific examples of the host compounds include carbazole, triazole, oxazole, oxadiazole, imidazole, polyarylalkane, pyrazoline, pyrazolone, phenylenediamine, arylamine, amino-substituted chalcone, styryl anthracene, fluorenone, hydrazone, stilbene and silazane derivatives; aromatic tertiary amine, styrylamine, aromatic dimethylidene and porphyrin compounds; anthraquinodimethane, anthrone, diphenylquinone, thiopyrandioxide, carbodiimide, fluoreniridenemethane and distyrylpyrazine derivatives; heterocyclic tetracarboxylic anhydrides such as naphthaleneperylene; phthalocyanine derivatives; metal complexes of 8-quinolinol derivatives; various metal complex polysilane compounds represented by metal complexes having metalphthalocyanine, benzoxazole or benzothiazole as a ligand; electroconductive macromolecular oligomers such as poly (N-vinylcarbazole) derivatives, aniline copolymers, thiophene oligomers and polythiophene; and macromolecular compounds such as polythiophene, polyphenylene, polyphenylenevinylene and polyfluorene derivatives. Host compounds can be used individually or as a combination of two or more kinds.

Specific compounds shown below can be exemplified.

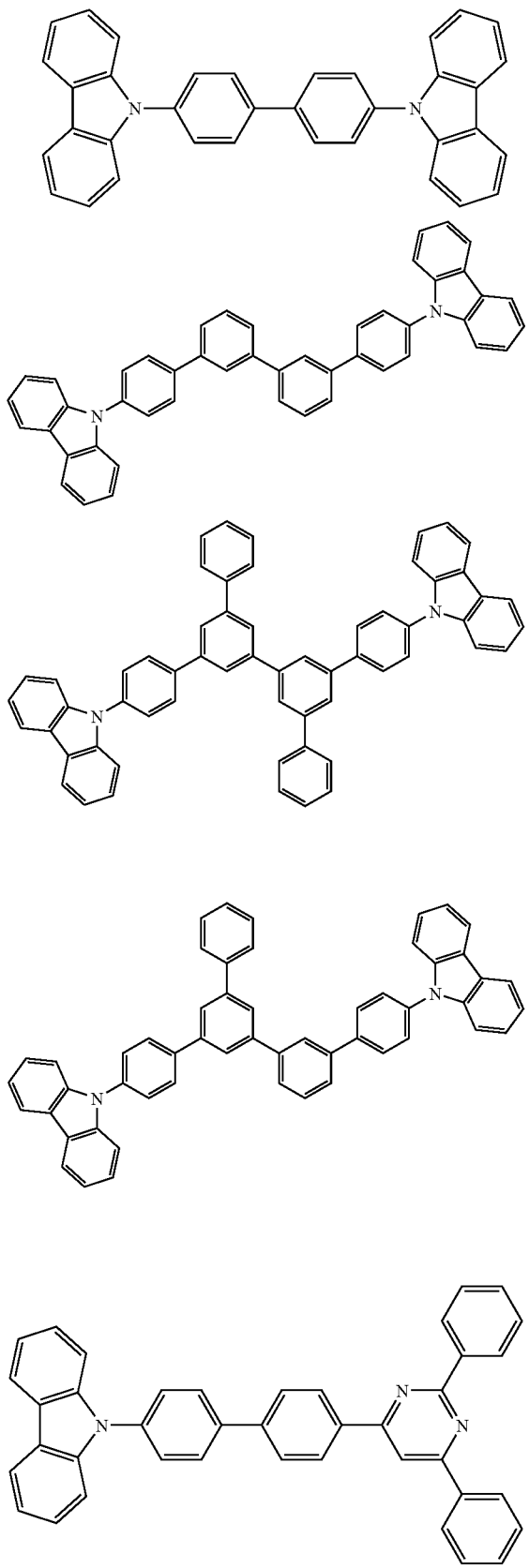

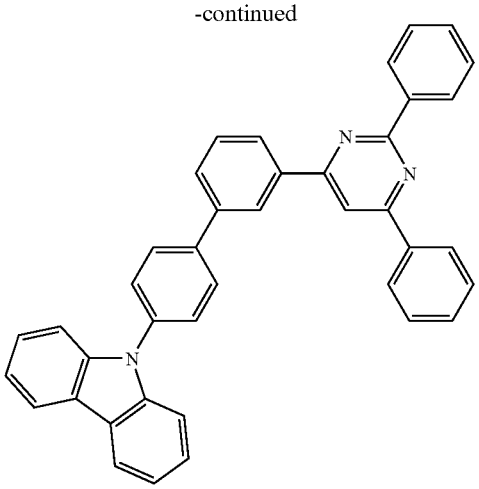

A phosphorescent dopant is a compound that can emit light from triplet excitons. The dopant is not limited so long as it can emit light from triplet excitons, but it is preferably a metal complex containing at least one metal selected from the group of Ir, Ru, Pd, Pt, Os and Re. A porphyrin metal complex or an ortho-metalated metal complex is preferable. As a porphyrin metal complex, a porphyrin platinum complex is preferable. The phosphorescent compounds can be used individually or as a combination of two or more kinds.

There are various ligands forming an ortho-metalated metal complex. Preferable ligands include 2-phenylpyridine, 7,8-benzoquinoline, 2-(2-thienyl)pyridine, 2-(1-naphtyl)pyridine and 2-phenylquinoline derivatives. These derivatives may have substituents, if necessary. Fluorides and derivatives with a trifluoromethyl group introduced are particularly preferable as a blue dopant. As an auxiliary ligand, ligands other than the above-mentioned ligands, such as acetylacetonate and picric acid may be contained.

The content of a phosphorescent dopant in an emitting layer is not limited and can be properly selected according to purposes; for example, it is 0.1 to 70 mass %, preferably 1 to 30 mass %. When the content of a phosphorescent compound is less than 0.1 mass %, emission may be weak and the advantages thereof may not be sufficiently obtained. When the content exceeds 70 mass %, the phenomenon called concentration quenching may significantly proceed, thereby degrading the device performance.

The emitting layer may contain hole-transporting materials, electron-transporting materials and polymer binders, if necessary.

The thickness of an emitting layer is preferably from 5 to 50 nm, more preferably from 7 to 50 nm and most preferably from 10 to 50 nm. When it is less than 5 nm, the formation of an emitting layer and the adjustment of chromaticity may become difficult. When it exceeds 50 nm, the driving voltage may increase.

(Hole-Transporting Layer: Hole-Injecting Layer)

The hole-transporting layer is a layer for helping the injection of holes into the emitting layer so as to transport holes to an emitting region. The hole mobility thereof is large and the ionization energy thereof is usually as small as 5.5 eV or less. Such a hole-transporting layer is preferably made of a material which can transport holes to the emitting layer at a low electric field intensity. In addition, for example, it is preferred that the hole mobility be at least $10^{-4}$ cm$^2$/V sec when an electric field of $10^4$ to $10^6$ V/cm is impressed.

Specific examples of materials for a hole-transporting layer include triazole derivatives (see U.S. Pat. No. 3,112,197 and others), oxadiazole derivatives (see U.S. Pat. No. 3,189,447 and others), imidazole derivatives (see JP-B-37-16096 and others), polyarylalkane derivatives (see U.S. Pat. Nos. 3,615,402, 3,820,989 and 3,542,544, JP-B-45-555 and 51-10983, JP-A-51-93224, 55-17105, 56-4148, 55-108667, 55-156953 and 56-36656, and others), pyrazoline derivatives and pyrazolone derivatives (see U.S. Pat. Nos. 3,180,729 and 4,278,746, JP-A-55-88064, 55-88065, 49-105537, 55-51086, 56-80051, 56-88141, 57-45545, 54-112637 and 55-74546, and others), phenylene diamine derivatives (see U.S. Pat. No. 3,615,404, JP-B-51-10105, 46-3712 and 47-25336, and 54-119925, and others), arylamine derivatives (see U.S. Pat. Nos. 3,567,450, 3,240,597, 3,658,520, 4,232,103, 4,175,961 and 4,012,376, JP-B-49-35702 and 39-27577, JP-A-55-144250, 56-119132 and 56-22437, DE1,110,518, and others), amino-substituted chalcone derivatives (see U.S. Pat. No. 3,526,501, and others), oxazole derivatives (ones disclosed in U.S. Pat. No. 3,257,203, and others), styrylanthracene derivatives (see JP-A-56-46234, and others), fluorenone derivatives (JP-A-54-110837, and others), hydrazone derivatives (see U.S. Pat. No. 3,717,462, JP-A-54-59143, 55-52063, 55-52064, 55-46760, 57-11350, 57-148749 and 2-311591, and others), stilbene derivatives (see JP-A-61-210363, 61-228451, 61-14642, 61-72255, 62-47646, 62-36674, 62-10652, 62-30255, 60-93455, 60-94462, 60-174749 and 60-175052, and others), silazane derivatives (U.S. Pat. No. 4,950,950), polysilanes (JP-A-2-204996), aniline copolymers (JP-A-2-282263), and electroconductive high molecular oligomers (in particular thiophene oligomers).

In addition to the hole-transporting layer, in order to help the injection of holes, it is preferred that the hole-injecting layer be provided separately. As the material for the hole-injecting layer, the organic EL material of the invention may be used singly or in combination with other materials. As the other materials, the same materials as used for the hole-transporting layer can be used. The following can also be used: porphyrin compounds (ones disclosed in JP-A-63-295695 and others), aromatic tertiary amine compounds and styrylamine compounds (see U.S. Pat. No. 4,127,412, JP-A-53-27033, 54-58445, 55-79450, 55-144250, 56-119132, 61-295558, 61-98353 and 63-295695, and others).

The following can also be given as examples: 4,4'-bis(N-(1-naphthyl)-N-phenylamino)biphenyl (NPD), which has in the molecule thereof two condensed aromatic rings, disclosed in U.S. Pat. No. 5,061,569, and 4,4',4''-tris(N-(3-methylphenyl)-N-phenylamino)triphenylamine (MTDATA), wherein three triphenylamine units are linked in a star-burst form, disclosed in JP-A-4-308688.

Inorganic compounds such as p-type Si and p-type SiC as well as aromatic dimethylidene type compounds can also be used as the material of the hole-injecting layer.

The hole-injecting layer or the hole-transporting layer can be formed, for example, by forming the above-mentioned compounds into a thin film by a known method such as vacuum vapor deposition, spin coating, casting or LB technique. The film thickness of the hole-injecting layer and hole-transporting layer is not particularly limited, and is usually from 1 nm to 5 μm. The hole-injecting layer or hole-transporting layer may be a single layer made of one or two or more of the above-mentioned materials, or may be stacked hole-injecting layers or hole-transporting layers made of different compounds, insofar as the compound of the invention is contained in the hole-transporting region.

An organic semiconductor layer is one type of a hole-transporting layer for helping the injection of holes or electrons into an emitting layer, and is preferably a layer having an electric conductivity of $10^{-10}$ S/cm or more. As the material of such an organic semiconductor layer, electroconductive oligomers such as thiophene-containing oligomers or arylamine-containing oligomers disclosed in JP-A-8-193191, and electroconductive dendrimers such as arylamine-containing dendrimers may be used.

(Electron-Injecting/Transporting Layer)

The electron-injecting/transporting layer is a layer which assists injection of electrons into the emitting layer and transports electrons to the emitting region, and exhibits a high degree of electron mobility. An adhesion-improving layer is the electron-injecting layer formed of a material which exhibits excellent adhesion to the cathode.

The thickness of the electron-transporting layer is arbitrarily selected in the range of several nanometers to several micrometers. When the electron-transporting layer has a large thickness, it is preferable that the electron mobility be at least $10^{-5}$ cm$^2$/Vs or more at an applied electric field of $10^4$ to $10^6$ V/cm in order to prevent an increase in voltage.

The material used in the electron-injecting layer is preferably 8-hydroxyquinoline or a metal complex of a derivative thereof or an oxadiazole derivative. As specific examples of 8-hydroxyquinoline and a metal complex of an 8-hydroxyquinoline derivative, metal chelate oxinoid compounds including a chelate of oxine (8-quinolinol or 8-hydroxyquinoline) can be given. For example, tris(8-quinolinol)aluminum can be used as the electron-injecting material.

An electron-transporting compound of the following general formula can be given as the oxadiazole derivative.

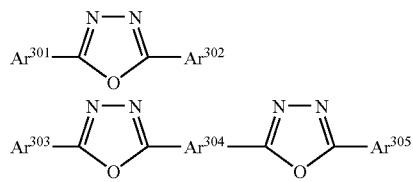

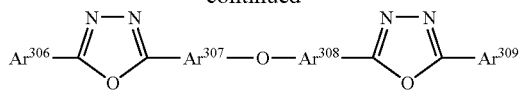

wherein $Ar^{301}$, $Ar^{302}$, $Ar^{303}$, $Ar^{305}$, $Ar^{306}$ and $Ar^{309}$ are independently substituted or unsubstituted aryl groups; and $Ar^{304}$, $Ar^{307}$ and $Ar^{308}$ are independently substituted or unsubstituted arylene groups.

As examples of the aryl group, a phenyl group, a biphenyl group, an anthranyl group, a perylenyl group, and a pyrenyl group can be given. As examples of the arylene group, a phenylene group, a naphthylene group, a biphenylene group, an anthranylene group, a perylenylene group, a pyrenylene group, and the like can be given. As the substituent, an alkyl group having 1 to 10 carbon atoms, an alkoxy group having 1 to 10 carbon atoms, a cyano group, and the like can be given. The electron-transporting compound is preferably one from which a thin film can be formed.

The following compounds can be given as specific examples of the electron-transporting compound.

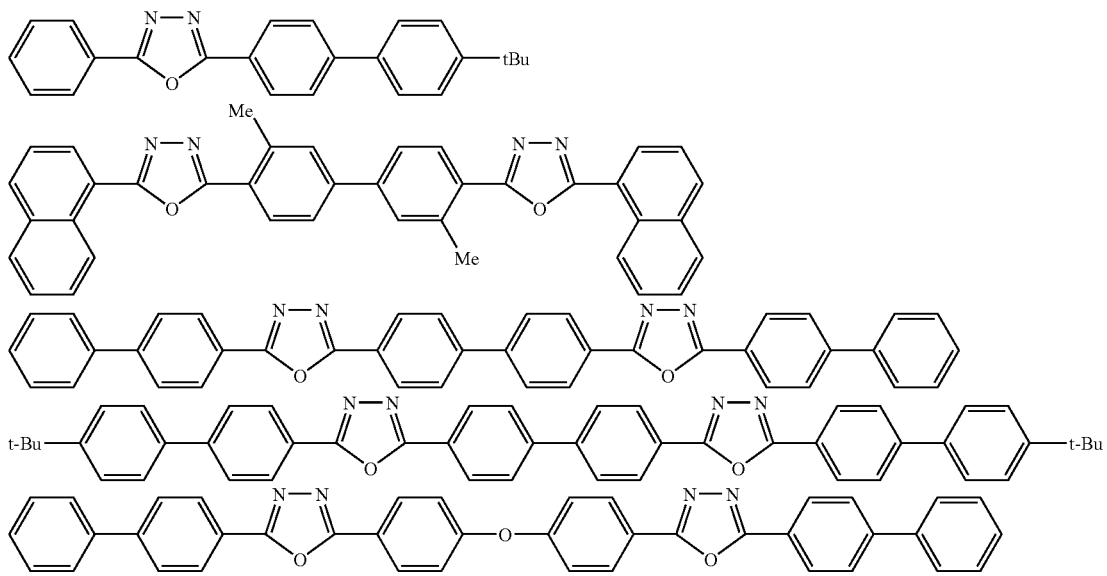

(Me is Methyl and tBu is T-Butyl)

Furthermore, as materials used for the electron-injecting layer and electron-transporting layer, the compounds shown by the following formulas (A) to (F) may be used.

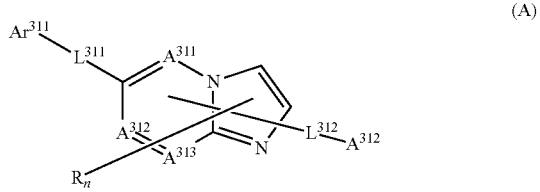

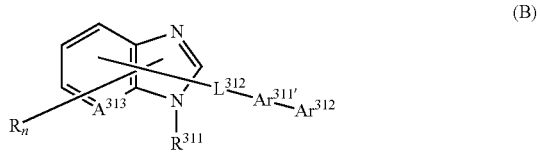

Nitrogen-containing heterocyclic ring derivatives shown by the formulas (A) and (B), wherein $A^{311}$ to $A^{313}$ are independently a nitrogen atom or a carbon atom;

$Ar^{311}$ is a substituted or unsubstituted aryl group having 6 to 60 ring carbon atoms or a substituted or unsubstituted heteroaryl group having 3 to 60 ring atoms; $Ar^{311'}$ is a substituted or unsubstituted arylene group having 6 to 60 ring carbon atoms or a substituted or unsubstituted heteroarylene group having 3 to 60 ring atoms; $Ar^{312}$ is a hydrogen atom, a substituted or unsubstituted aryl group having 6 to 60 ring carbon atoms, a substituted or unsubstituted heteroaryl group having 3 to 60 ring atoms, a substituted or unsubstituted alkyl group having 1 to 20 carbon atoms, or a substituted or unsubstituted alkoxy group having 1 to 20 carbon atoms, provided that one of $Ar^{311}$ and $Ar^{312}$ is a substituted or unsubstituted condensed ring group having 10 to 60 ring carbon atoms, or a substituted or unsubstituted monohetero condensed ring group having 3 to 60 ring atoms;

$L^{311}$, $L^{312}$ and $L^{313}$ are independently a single bond, a substituted or unsubstituted arylene group having 6 to 60 ring carbon atoms, a substituted or unsubstituted heteroarylene group having 3 to 60 ring atoms or a substituted or unsubstituted fluorenylene group; and R and $R^{311}$ are independently a hydrogen atom, a substituted or unsubstituted aryl group having 6 to 60 ring carbon atoms, a substituted or unsubstituted heteroaryl group having 3 to 60 ring atoms, a substituted or unsubstituted alkyl group having 1 to 20 carbon atoms, or a substituted or unsubstituted alkoxy group having 1 to 20 carbon atoms, and n is an integer of 0 to 5, provided that, when n is an integer of 2 or more, a plurality of Rs may be the same or different; adjacent Rs may be bonded to form a carbocyclic aliphatic ring or a carbocyclic aromatic ring.

A nitrogen-containing heterocyclic derivative shown by the formula (C):

HAr-$L^{314}$-$Ar^{321}$-$Ar^{322}$    (C)

wherein HAr is a nitrogen-containing heterocyclic ring with 3 to 40 carbon atoms which may have a substituent; $L^{314}$ is a single bond, an arylene group with 6 to 60 carbon atoms which may have a substituent, a heteroarylene group with 3 to 60 atoms which may have a substituent or a fluorenylene group which may have a substituent; $Ar^{321}$ is a divalent aromatic hydrocarbon group with 6 to 60 carbon atoms which may have a substituent; and $Ar^{322}$ is an aryl group with 6 to 60 carbon atoms which may have a substituent or a heteroaryl group with 3 to 60 atoms which may have a substituent.

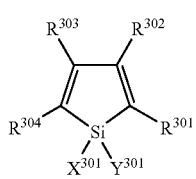

(D)

Silacyclopentadiene derivatives shown by the above formula (D) wherein $X^{301}$ and $Y^{301}$ are independently a saturated or unsaturated hydrocarbon group having 1 to 6 carbon atoms, an alkoxy group, an alkenyloxy group, an alkynyloxy group, a hydroxyl group, a substituted or unsubstituted aryl group, or a substituted or unsubstituted hetero ring, or X and Y are bonded to form a saturated or unsaturated ring, and $R^{301}$ to $R^{304}$ are independently a hydrogen atom, a halogen atom, an alkyl group, an alkoxy group, an aryloxy group, a perfluoroalkyl group, a perfluoroalkoxy group, an amino group, an alkylcarbonyl group, an arylcarbonyl group, an alkoxycarbonyl group, an aryloxycarbonyl group, an azo group, an alkylcarbonyloxy group, an arylcarbonyloxy group, an alkoxycarbonyloxy group, an aryloxycarbonyloxy group, a sulfinyl group, a sulfonyl group, a sulfanyl group, a silyl group, a carbamoyl group, an aryl group, a heterocyclic group, an alkenyl group, an alkynyl group, a nitro group, a formyl group, a nitroso group, a formyloxy group, an isocyano group, a cyanate group, an isocyanate group, a thiocyanate group, an isothiocyanate group, or a cyano group, these groups may be substituted, or adjacent groups of $R^{301}$ to $R^{304}$ may form a substituted or unsubstituted condensed ring.

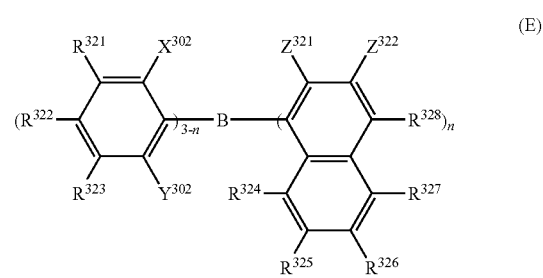

(E)

Borane derivatives shown by the above formula E: wherein $R^{321}$ to $R^{328}$ and $Z^{322}$ are independently a hydrogen atom, a saturated or unsaturated hydrocarbon group, an aromatic hydrocarbon group, a heterocyclic group, a substituted amino group, a substituted boryl group, an alkoxy group, or an aryloxy group, $X^{302}$, $Y^{302}$, and $Z^{321}$ are independently a saturated or unsaturated hydrocarbon group, an aromatic hydrocarbon group, a heterocyclic group, a substituted amino group, an alkoxy group, or an aryloxy group, $Z^{321}$ and $Z^{322}$ may be bonded to each other to form a condensed ring; n is an integer of 1 to 3; and when n or (3−n) is 2 or more, $R^{321}$ to $R^{328}$, $X^{302}$, $Y^{302}$, $Z^{322}$ and $Z^{321}$ may be the same or different, provided that a case in which n is 1, X, Y and $R^{322}$ are methyl groups, and $R^{328}$ is a hydrogen atom or a substituted boryl-containing compound, and a case in which n is 3 and $Z^{321}$ is a methyl-containing compound are excluded.

(F)

Gallium complex shown by the above formula F:

wherein $Q^{301}$ and $Q^{302}$ are independently ligands shown by the following formula (K) and $L^{315}$ is a halogen atom, a substituted or unsubstituted alkyl group, a substituted or unsubstituted cycloalkyl group, a substituted or unsubstituted aryl group, a substituted or unsubstituted heterocyclic group, —OR (R is a hydrogen atom, a substituted or unsubstituted alkyl group, a substituted or unsubstituted cycloalkyl group, a substituted or unsubstituted aryl group, or a substituted or unsubstituted heterocyclic group) or a ligand shown by —O—Ga-$Q^{303}$($Q^{304}$) ($Q^{303}$ and $Q^{304}$ have the same meanings as $Q^{301}$ and $Q^{302}$).

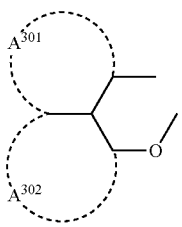

(K)

wherein rings $A^{301}$ and $A^{302}$ are independently a 6-membered aryl ring structure which may have a substituent, and are condensed to each other.

The metal complexes have the strong nature of an n-type semiconductor and large ability of injecting electrons. Furthermore, the energy generated at the time of forming a complex is small so that a metal is then strongly bonded to ligands in the complex formed and the fluorescent quantum efficiency becomes large as the emitting material.

Specific examples of the substituents for the rings $A^{301}$ and $A^{302}$ forming the ligand of the above formula (K) include halogen atoms such as chlorine, bromine, iodine, and fluorine, substituted or unsubstituted alkyl groups such as a methyl group, ethyl group, propyl group, butyl group, sec-butyl group, tert-butyl group, pentyl group, hexyl group, heptyl group, octyl group, stearyl group, and trichloromethyl group, substituted or unsubstituted aryl groups such as a phenyl group, naphthyl group, biphenyl group, anthranyl group, phenanthryl group, fluorenyl group, pyrenyl group, 3-methylphenyl group, 3-methoxyphenyl group, 3-fluorophenyl group, 3-trichloromethylphenyl group, 3-trifluoromethylphenyl group, and 3-nitrophenyl group, substituted or unsubstituted alkoxy groups such as a methoxy group, n-butoxy group, tert-butoxy group, trichloromethoxy group, trifluoroethoxy group, pentafluoropropoxy group, 2,2,3,3-tetrafluoropropoxy group, 1,1,1,3,3,3-hexafluoro-2-propoxy group, and 6-(perfluoroethyl)hexyloxy group, substituted or unsubstituted aryloxy groups such as a phenoxy group, p-nitrophenoxy group, p-tert-butylphenoxy group, 3-fluorophenoxy group, pentafluorophenyl group, and 3-trifluoromethylphenoxy group, substituted or unsubstituted alkylthio groups such as a methylthio group, ethylthio group, tert-butylthio group, hexylthio group, octylthio group, and trifluoromethylthio group, substituted or unsubstituted arylthio groups such as a phenylthio group, p-nitrophenylthio group, p-tert-butylphenylthio group, 3-fluorophenylthio group, pentafluorophenylthio group, and 3-trifluoromethylphenylthio group, a cyano group, a nitro group, an amino group, mono- or di-substituted amino groups such as a methylamino group, dimethylamino group, ethylamino group, diethylamino group, dipropylamino group, dibutylamino group, and diphenylamino group, acylamino groups such as a bis(acetoxymethyl)amino group, bis(acetoxyethyl)amino group, bis(acetoxypropyl)amino group, and bis(acetoxybutyl)amino group, a hydroxyl group, a siloxy group, an acyl group, substituted or unsubstituted carbamoyl groups such as a carbamoyl group, methylcarbamoyl group, dimethylcarbamoyl group, ethylcarbamoyl group, diethylcarbamoyl group, propylcarbamoyl group, butylcarbamoyl group, and phenylcarbamoyl group, a carboxylic acid group, a sulfonic acid group, an imide group, cycloalkyl groups such as a cyclopentane group and a cyclohexyl group, heterocyclic groups such as a pyridinyl group, pyrazinyl group, pyrimidinyl group, pyridazinyl group, triazinyl group, indolinyl group, quinolinyl group, acridinyl group, pyrrolidinyl group, dioxanyl group, piperidinyl group, morphorinyl group, piperazinyl group, carbazolyl group, furanyl group, thiophenyl group, oxazolyl group, oxadiazolyl group, benzoxazolyl group, thiazolyl group, thiadiazolyl group, benzothiazolyl group, triazolyl group, imidazolyl group, benzoimidazolyl group, and the like. The above substituents may be bonded to form a further six-membered aryl ring or heterocyclic ring.

A preferred embodiment of the organic EL device is a device containing a reducing dopant in an electron-transporting region or in an interfacial region between the cathode and the organic layer. The reducing dopant is defined as a substance which can reduce an electron-transporting compound. Accordingly, various substances which have given reducing properties can be used. For example, at least one substance can be preferably used which is selected from the group comprising alkali metals, alkaline earth metals, rare earth metals, alkali metal oxides, alkali metal halides, alkaline earth metal oxides, alkaline earth metal halides, rare earth metal oxides, rare earth metal halides, alkali metal carbonate, alkaline earth metal carbonate, rare earth metal carbonate, alkali metal organic complexes, alkaline earth metal organic complexes, and rare earth metal organic complexes.

More specific examples of the preferred reducing dopants include at least one alkali metal selected from the group comprising Li (work function: 2.9 eV), Na (work function: 2.36 eV), K (work function: 2.28 eV), Rb (work function: 2.16 eV) and Cs (work function: 1.95 eV), and at least one alkaline earth metal selected from the group comprising Ca (work function: 2.9 eV), Sr (work function: 2.0 to 2.5 eV), and Ba (work function: 2.52 eV). A reducing dopant having a work function of 2.9 eV or less is particularly preferable.

Among these, a more preferable reducing dopant is at least one alkali metal selected from the group comprising K, Rb and Cs. Even more preferable is Rb or Cs. Most preferable is Cs.

These alkali metals are particularly high in reducing ability. Thus, the addition of a relatively small amount thereof to an electron-injecting zone improves the luminance of the organic EL device and makes the lifetime thereof long. As a reducing dopant having a work function of 2.9 eV or less, combinations of two or more alkali metals mentioned above are preferable, particularly combinations including Cs, such as Cs and Na, Cs and K, Cs and Rb, or Cs, Na and K are preferable.

The combination containing Cs makes it possible to exhibit the reducing ability efficiently. The luminance of the organic EL device can be improved and the lifetime thereof can be made long by the addition of the reducing agent to its electron-injecting zone.

In the invention, an electron-injecting layer made of an insulator or a semiconductor may further be provided between a cathode and an organic layer. By forming the electron-injecting layer, current leakage can be effectively prevented and electron-injecting properties can be improved.

As the insulator, at least one metal compound selected from the group comprising alkali metal calcogenides, alkaline earth metal calcogenides, alkali metal halides and alkaline earth metal halides can be preferably used. When the electron-injecting layer is formed of the alkali metal calcogenide or the like, the injection of electrons can be preferably further improved.

Specifically preferable alkali metal calcogenides include $Li_2O$, LiO, $Na_2S$, $Na_2Se$ and NaO and preferable alkaline earth metal calcogenides include CaO, BaO, SrO, BeO, BaS and CaSe. Preferable alkali metal halides include LiF, NaF, KF, CsF, LiCl, KCl and NaCl. Preferable alkaline earth metal halides include fluorides such as $CaF_2$, $BaF_2$, $SrF_2$, $MgF_2$ and $BeF_2$ and halides other than fluorides.

Semiconductors forming an electron-transporting layer include one or combinations of two or more of oxides, nitrides, and oxidized nitrides containing at least one element of Ba, Ca, Sr, Yb, Al, Ga, In, Li, Na, Cd, Mg, Si, Ta, Sb and Zn.

An inorganic compound forming an electron-transporting layer is preferably a microcrystalline or amorphous insulating thin film. When the electron-transporting layer is formed of the insulating thin films, more homogeneous thin film is formed, whereby pixel defects such as a dark spot are decreased.

Examples of such an inorganic compound include the above-mentioned alkali metal calcogenides, alkaline earth metal calcogenides, alkali metal halides and alkaline earth metal halides.

(Cathode)

For the cathode, the following may be used: an electrode substance made of a metal, an alloy or an electroconductive compound, or a mixture thereof which has a small work function (for example, 4 eV or less). Specific examples of the electrode substance include sodium, sodium-potassium alloy, magnesium, lithium, magnesium/silver alloy, aluminum/aluminum oxide, aluminum/lithium alloy, indium, and rare earth metals.

This cathode can be formed by making the electrode substances into a thin film by vapor deposition, sputtering or some other method.

In the case where emission from the emitting layer is outcoupled through the cathode, the cathode preferably has a light transmittance of larger than 10%.

The sheet resistance of the cathode is preferably several hundred $\Omega/\square$ or less, and the film thickness thereof is usually from 10 nm to 1 µm, preferably from 50 to 200 nm.

(Insulating Layer)

In the organic EL device, pixel defects based on leakage or a short circuit are easily generated since an electric field is applied to the ultrathin film. In order to prevent this, it is preferred that an insulative thin film layer be inserted between the pair of electrodes.

Examples of the material used in the insulating layer include aluminum oxide, lithium fluoride, lithium oxide, cesium oxide, magnesium oxide, magnesium fluoride, calcium oxide, calcium fluoride, cesium fluoride, cesium carbonate, aluminum nitride, titanium oxide, silicon oxide, germanium oxide, silicon nitride, boron nitride, molybdenum oxide, ruthenium oxide, and vanadium oxide.

A mixture or laminate thereof may be used.

(Example of Fabricating an Organic EL Device)

Using the above-mentioned materials, an organic EL device can be fabricated by forming an anode, a hole-injecting layer, a hole-transporting layer, an emitting layer, an electron-injecting layer or the like, followed by formation of a cathode. The organic EL device can be fabricated in the order reverse to the above, i.e., the order from a cathode to an anode.

An example of the fabrication of the organic EL device will be described below which has a structure wherein the following are successively formed on a transparent substrate: anode/hole-injecting layer/hole-transporting layer/emitting layer/electron-transporting layer/cathode.

First, a thin film made of an anode material is formed into a thickness of 1 µm or less, preferably 10 to 200 nm on an appropriate transparent substrate by vapor deposition, sputtering or some other method, thereby forming an anode.

Next, a hole-injecting layer and a hole-transporting layer are formed on this anode. As described above, these layers can be formed by vacuum deposition, spin coating, casting, LB technique, or some other method. Vapor vacuum deposition is preferred since a homogenous film is easily obtained and pinholes are not easily generated.

In the case where the hole-injecting layer and the hole-transporting layer are formed by vacuum vapor deposition, conditions for the deposition vary depending upon the compound used, the desired crystal structure or recombining structure of the hole-injecting layer and the hole-transporting layer, and others. In general, the conditions are preferably selected from the following: deposition source temperature of 50 to 450° C., vacuum degree of $10^{-7}$ to $10^{-3}$ torr, vapor deposition rate of 0.01 to 50 nm/second, substrate temperature of −50 to 300° C., and film thickness of 1 nm to 5 µm.

Next, an emitting layer is formed on the hole-transporting layer. The emitting layer can also be formed by making a desired organic luminescent material into a thin film by vacuum vapor deposition, sputtering, spin coating, casting or some other method. Vacuum vapor deposition is preferred since a homogenous film is easily obtained and pinholes are not easily generated. In the case where the emitting layer is formed by vapor vacuum deposition, conditions for the deposition, which vary depending on a compound used, can be generally selected from conditions similar to those for the hole-transporting layer.

Next, an electron-transporting layer is formed on this emitting layer. Like the hole-transporting layer and the emitting layer, the layer is preferably formed by vacuum vapor deposition because a homogenous film is required. Conditions for the deposition can be selected from conditions similar to those for the hole-transporting layer and the emitting layer.

Lastly, a cathode is stacked thereon to obtain an organic EL device.

The cathode is made of a metal, and vapor deposition or sputtering may be used. However, vapor vacuum deposition is preferred in order to protect underlying organic layers from being damaged when the cathode film is formed.

For the organic EL device fabrication that has been described above, it is preferred that the formation from the anode to the cathode is continuously carried out, using only one vacuuming operation.

The method for forming each of the layers in the organic EL device of the invention is not particularly limited. Specifically, the layers can be formed by a known method, such as vacuum deposition, molecular beam epitaxy (MBE method), or coating method such as dipping, spin coating, casting, bar coating and roll coating using a solution obtained by dissolving materials in a solvent.

The film thickness of each of the organic layers in the organic EL device of the invention is not particularly limited. In general, defects such as pinholes are easily generated when the film thickness is too small. Conversely, when the film thickness is too large, a high applied voltage becomes necessary, leading to low efficiency. Usually, the film thickness is preferably in the range of several nanometers to one micrometer.

The organic EL device emits light when applying a voltage between electrodes. If a DC voltage is applied to the organic EL device, emission can be observed when the polarities of the anode and the cathode are positive and negative, respectively, and a DC voltage of 5 to 40 V is applied. When a voltage with an opposite polarity is applied, no electric current flows and hence, emission does not occur. If an AC voltage is applied, uniform emission can be observed only when the anode and the cathode have a positive polarity and a negative polarity, respectively. The waveform of the AC applied may be arbitrary.

EXAMPLES

The material for an organic EL device and the organic EL device of the invention will be described below in more detail with reference to Examples, which should not be construed as limiting the scope of the invention.

The structures of the compounds synthesized or used in the examples are shown below.

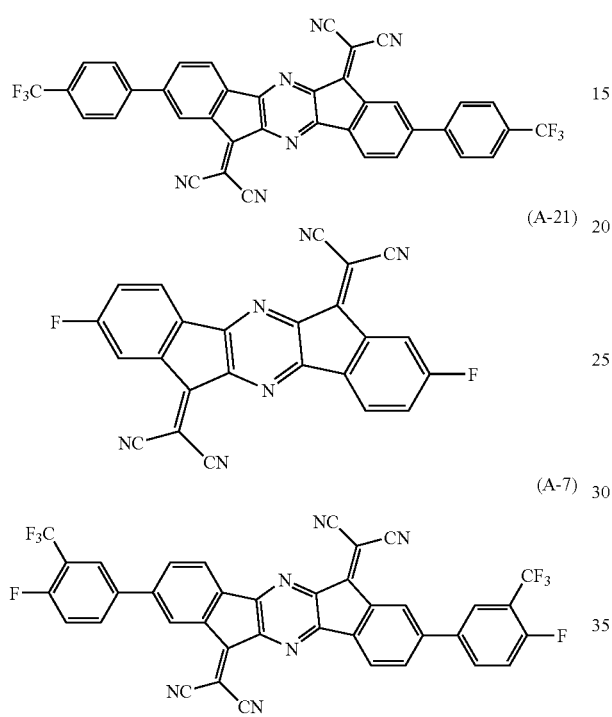

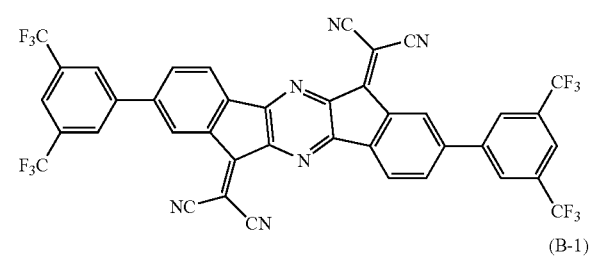

Example 1

Synthesis of a Compound Shown by the Formula (A-1)

The compound (A-1) was synthesized by the following synthesis scheme.

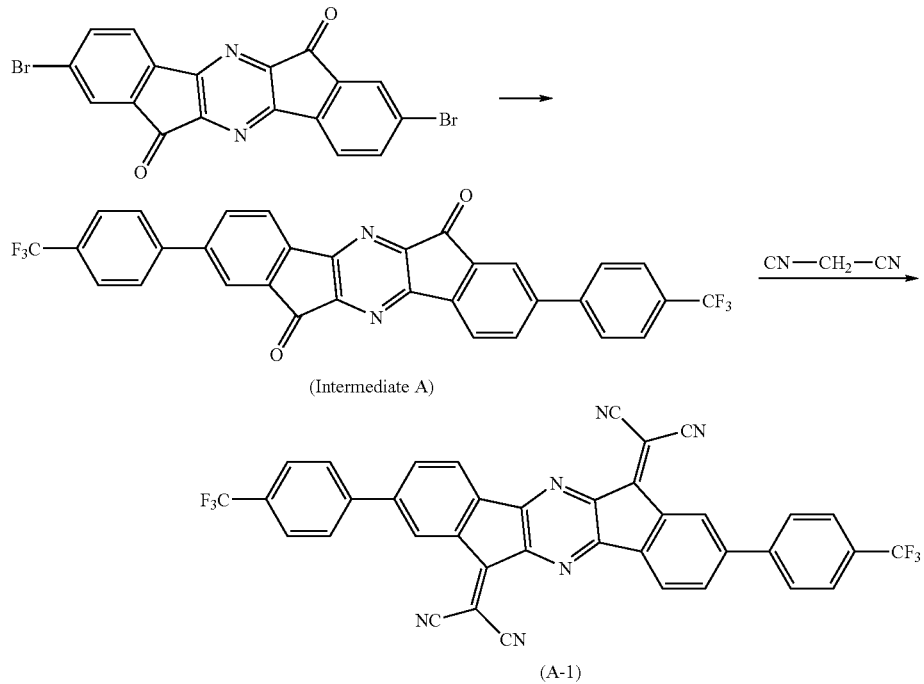

(1) Synthesis of (Intermediate A)

2.2 g of 2,8-dibromo-diindenopyrazine-6,12-dione which had been synthesized in accordance with the synthesis method described in a document (Chemische Berichte (1956), vol. 89, page 2799) was mixed with 2.1 g of 4-(trifluoromethyl)phenylboronic acid, 0.14 g of tris(dibenzylideneacetone)dipalladium (0), 0.091 g of tris-t-butylphosphine, 1.9 g of potassium fluoride and 50 ml of THF under argon stream. The mixture was stirred under reflux for 8 hours. After cooling, the reaction liquid was filtered and a red purple solid was washed with water and methanol, whereby 1.7 g of the solid was obtained. As a result of mass spectroscopy of the resulting solid, a peak was observed at M/Z=572.

As a result of the $^1$H-NMR measurement, a spectrum derived from the trifluoromethylphenyl group was observed at around 7.8 to 8.2 ppm.

(2) Synthesis of (A-1)

1.4 g of the intermediate A which had been synthesized above, 0.35 g of malononitrile and 80 ml of pyridine were added, and the resultant was stirred at room temperature for 24 hours. The solid matter was filtered, washed with water and methanol, and dried under reduced pressure. Thereafter, purification through sublimation was performed (sublimation temperature: 340° C.) to obtain 1.1 g of a purple crystal.

The IR of this compound was measured. The results showed that the absorption of a carbonyl group at 1732 cm$^{-1}$ disappeared and the absorption of a cyano group was newly observed at 2227 cm$^{-1}$. As a result of mass spectroscopy, a peak was observed at M/Z=668. Elementary analysis: C38H14F6N6, calculated value: C, 68.27; H, 2.11; N, 12.57, actually measured value: C, 68.55; H, 2.32; N, 12.35.

The compound was dissolved in acetonitrile with a concentration of 0.01 mol/l, and the reduction potential thereof was measured by cyclic voltammetry by using tetrabutylammonium perchlorate (TBAP) as a supporting electrolyte and a silver-silver chloride electrode as a reference electrode. The reduction potential of the compound (A-1) at a sweep rate of 0.1 V/s was +0.1 V.

As a reference material, ferrocene (hereinafter referred to as "Fc") was measured similarly. The first oxidation potential thereof was 0.5V. Taking this oxidation potential of ferrocene as a reference, the reduction potential of the compound (A-1) was −0.4 V(vs Fc$^+$/Fc).

Example 2

Synthesis of a Compound Shown by the Formula (A-21)

Synthesis was performed by the following synthesis scheme.

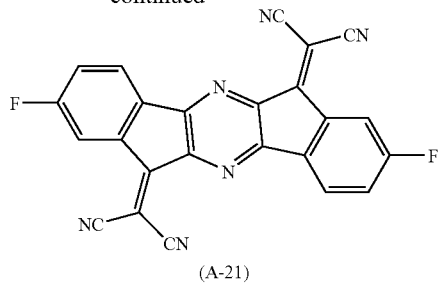

(A-21)

1.5 g of 2,8-difluoro-indenopyrazine-6,12-dione which had been synthesized in accordance with the synthesis method described in a document (Chemische Berichte (1956), vol. 89, page 2799) was mixed with 1.3 g of malononitrile and 100 ml of pyridine. The mixture was stirred under reflux for 12 hours. After cooling to room temperature, a dark purple crystal was filtered off and washed with hydrochloric acid and acetonitrile After purification of the solid through sublimation (sublimation temperature: 260° C.), 1.2 g of a compound was obtained.

The IR of this compound was measured. The results showed that the absorption of a carbonyl group at 1732 cm$^{-1}$ disappeared and the absorption of a cyano group was newly observed at 2228 cm$^{-1}$. As a result of mass spectroscopy, a peak was observed at M/Z=416. Elementary analysis: C24H6F2N6, calculated value: C, 69.24; H, 1.45; N, 20.19, actually measured value: C, 69.33; H, 1.49; N, 20.35.

The reduction potential of this compound was measured by the cyclic voltammetry as in Example 1. The reduction potential of the compound (A-21) was −0.4 V(vsFc$^+$/Fc).

Example 3

Synthesis of a Compound Shown by the Formulas (B-1) and (B-3)

Synthesis was performed by the following synthesis scheme.

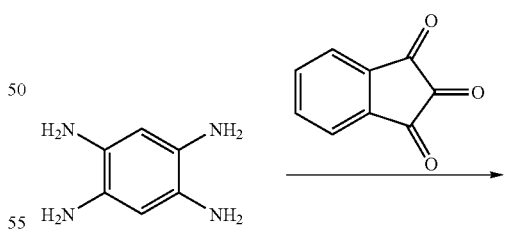

4 HCl

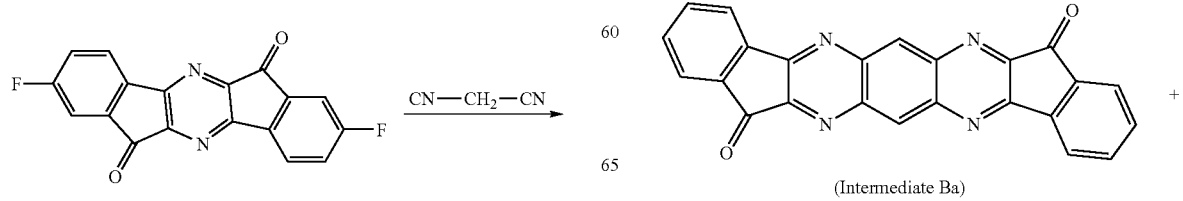

(Intermediate Ba)

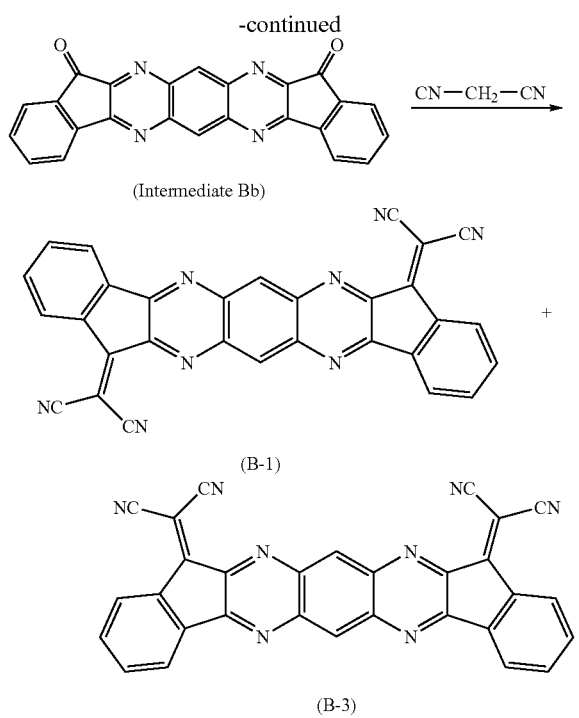

(Intermediate Bb)

(B-1)

(B-3)

(1) Synthesis of a Mixture of (Intermediate Ba) and (Intermediate BB)

To the mixture of 2.8 g of ninhydrin, 0.86 g of sodium acetate and 100 ml of ethanol with the mixture being stirred at room temperature, a solution of 1.5 g of 1,2,4,5-benzenetetramine tetrahydrochloride and 20 ml of ethanol was added dropwise. After the dropwise addition, stirring under reflux was performed for 2 hours. After cooling to room temperature, a deposited yellow solid was filtered off, washed with water and ethanol, and dried, whereby 1.8 g of a compound was obtained. As a result of mass spectroscopy of the resulting compound, a peak was observed at M/Z=386. As a result of the $^1$H-NMR measurement, a spectrum derived from the heteroaromatic ring was observed at 7.6 to 8.4 ppm. However, the mixture ratio of the compound (B-1) and the compound (B-3) could not be determined.

(1) Synthesis of a Mixture of (B-1) and (B-3)

0.3 g of malononitrile and 100 ml of pyridine was added to 1.7 g of the mixture of the (intermediate Ba) and the (intermediate Bb) which had been synthesized above, and the resultant was stirred under reflux for 12 hours. After cooling to room temperature, an orange crystal was filtered off, washed with hydrochloric acid, water and acetonitrile. The solid was purified through sublimation, whereby 1.5 g of a compound was obtained.

The IR of this compound was measured. The results showed that the absorption derived from a carbonyl group disappeared and the absorption of a cyano group was newly observed at 2290 cm$^{-1}$. As a result of mass spectroscopy, a peak was observed at M/Z=482. Elementary analysis: C30H10N8, calculated value: C, 74.69; H, 2.09; N, 23.23, actually measured value: C, 74.75; H, 2.25; N, 23.39.

The reduction potential of this compound was measured by the cyclic voltammetry as in Example 1. The reduction potential of the mixture of (B-1) and (B-3) was −0.9 V(vsFc$^+$/Fc).

Example 4

Synthesis of the Compound Shown by the Formula (A-7)

Synthesis was performed by the following synthesis scheme.

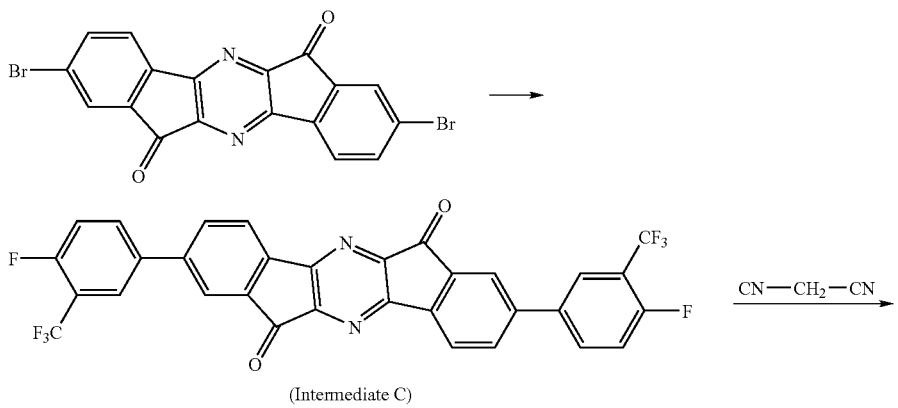

(Intermediate C)

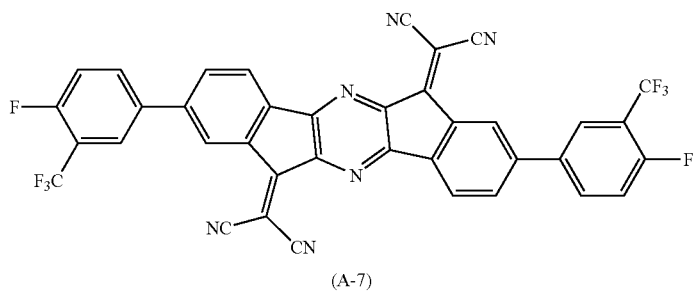

(A-7)

(1) Synthesis of (Intermediate C)

Synthesis was performed in the same manner as in the synthesis of the intermediate A in Example 1, except that 2.1 g of 4-(trifluoromethyl)phenylboronic acid was changed to 2.3 g of 4-fluoro-3-trifluoromethylphenylboronic acid (sublimation temperature: 330° C.), whereby 1.5 g of an orange solid was obtained. As a result of mass spectroscopy of the resulting solid, a peak was observed at M/Z=608.

As a result of the $^1$H-NMR measurement, a spectrum derived from the trifluoromethylphenyl group was observed at around 7.4 to 8.2 ppm.

(2) Synthesis of (A-7)

The same procedures as in the synthesis of (A-1) in Example 1 were performed except that 1.4 g of the intermediate A was changed to 1.5 g of the intermediate C which was synthesized above (sublimation temperature: 330° C.).

The IR of this compound was measured. The results showed that the absorption of a carbonyl group at 1730 cm$^{-1}$ disappeared and the absorption of a cyano group was newly observed at 2227 cm$^{-1}$. As a result of mass spectroscopy, a peak was observed at M/Z=704.

The reduction potential of this compound was measured by the cyclic voltammetry as in Example 1. The reduction potential of (A-7) was −0.4 V(vsFc$^+$/Fc)

Example 5

Synthesis of the Compound Shown by the Formula (A-33)

Synthesis was performed by the following synthesis scheme.

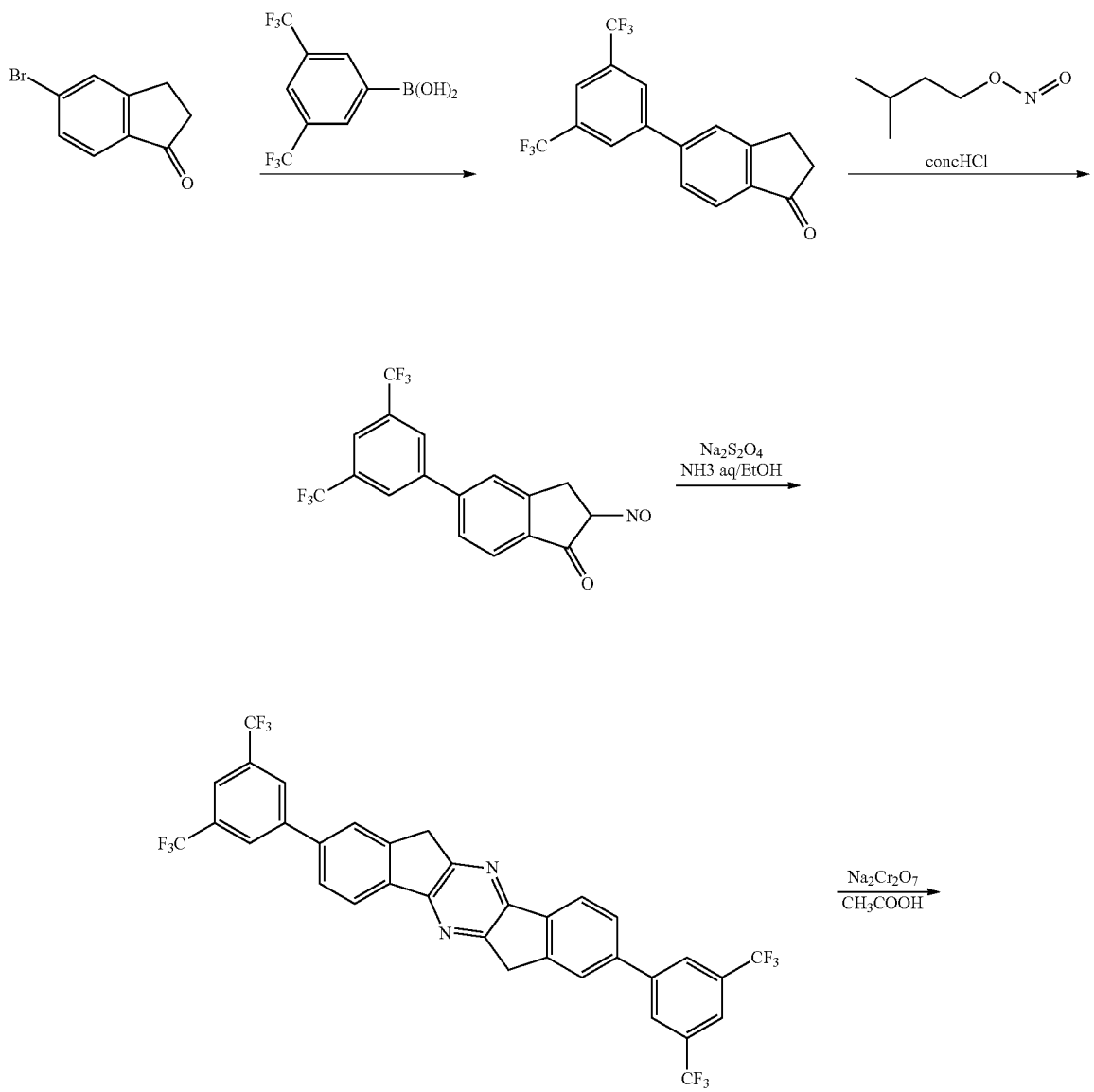

-continued

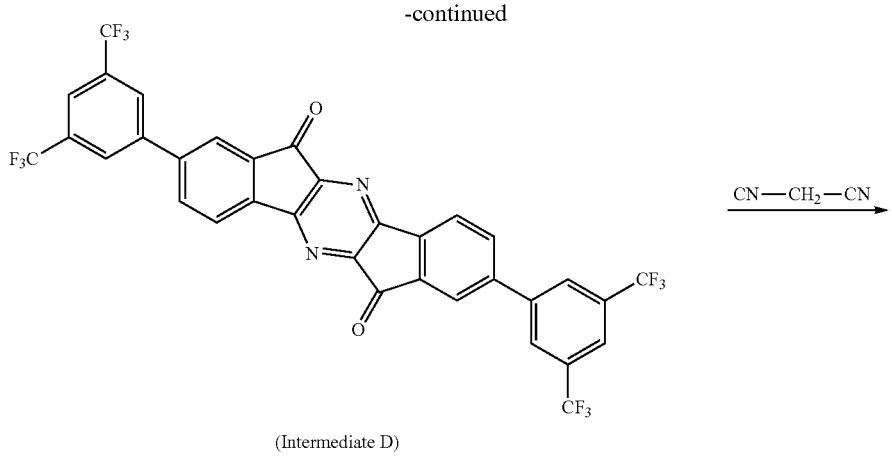

(Intermediate D)

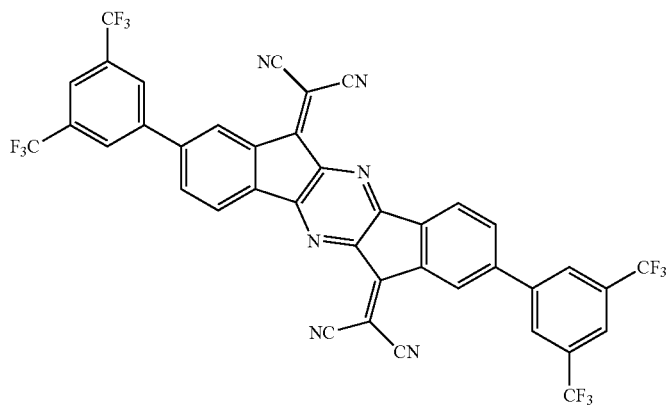

(A-33)

(1) Synthesis of (Intermediate D)

10 g of 5-bromo-1-indanone, 15 g of 3,5-bistrifluoromethylphenylboronic acid, 1.1 g of tetraxis(triphenylphosphine) palladium (0), 85 ml of 2M sodium carbonate and 120 ml of toluene were mixed. The resulting mixture was refluxed with stirring at 110° C. for 8 hours. After cooling, the reaction liquid was filtered, washed with water and methanol, and purified by means of a silica gel column (solvent: ethylene chloride), whereby 14 g of a white solid was obtained. As a result of mass spectroscopy, a peak was observed at M/Z=344. With reference to a document (Chemische Berichte (1956), vol. 89, page 2799), the solid was subjected to a nitrosation reaction, a cyclization reaction and an oxidation reaction, whereby 4 g of an orange solid was obtained. As a result of mass spectroscopy, a peak was observed at M/Z=680. Furthermore, the IR measurement of this solid confirmed the absorption of the carbonyl group at 1732 cm$^{-1}$.

(2) Synthesis of (A-33)

The same procedures as in the synthesis of (A-1) in Example 1 were performed except that 1.4 g of the intermediate A was changed to 1.6 g of the intermediate D (sublimation temperature 320° C.) which was synthesized above.

The IR of this compound was measured. The results showed that the absorption of a carbonyl group at 1732 cm$^{-1}$ disappeared and the absorption of a cyano group was newly observed at 2225 cm$^{-1}$. As a result of mass spectroscopy, a peak was observed at M/Z=804.

The reduction potential of this compound was measured by the cyclic voltammetry as in Example 1. The reduction potential of (A-33) was −0.35 V(vsFc$^+$/Fc).

[Organic EL Device]

Example 6

A glass substrate of 25 mm by 75 mm by 1.1 mm thick with an ITO transparent electrode (GEOMATEC CO., LTD.) was subjected to ultrasonic cleaning with isopropyl alcohol for 5 minutes, and cleaned with ultraviolet rays and ozone for 30 minutes.

The cleaned glass substrate having the transparent electrode lines was then secured to a substrate holder of an apparatus for vacuum vapor deposition. First, the compound shown by the formula (A-21) which has been synthesized in Example 2 and the compound shown by the following formula (C-1) were deposited onto the surface of the glass substrate on which the transparent electrode lines were formed so as to cover the transparent electrodes, thereby forming a 60 nm-thick film in which the compound shown by the formula (A-21) and the compound shown by the following formula (C-1) were mixed at a molar ratio of 2:98. The film of the compound mixture served as a hole-injecting layer.

Subsequently, a 20 nm-thick film of a compound shown by the following formula (HTM-1) was formed on the above-obtained film of the compound mixture. This film functioned as a hole-transporting layer.

Further, a compound shown by the following formula (EM1) with a film thickness of 40 nm was deposited thereon to form a film. Simultaneously, the below-mentioned amine compound having a styryl group (D1) was deposited such that the weight ratio of EM1 and D1 became 40:2. This film functioned as an emitting layer.

Alq was deposited to form a 10 nm thick film on the above-obtained film. The film served as an electron-injecting layer. Then, Li as a reducing dopant (Li source: manufactured by SAES Getters Co., Ltd.) and Alq were co-deposited, whereby an Alq:Li film (film thickness: 10 nm) was formed as an electron-injecting layer (cathode). Metal aluminum was deposited on the Alq:Li film to form a metallic cathode, whereby an organic EL device was fabricated.

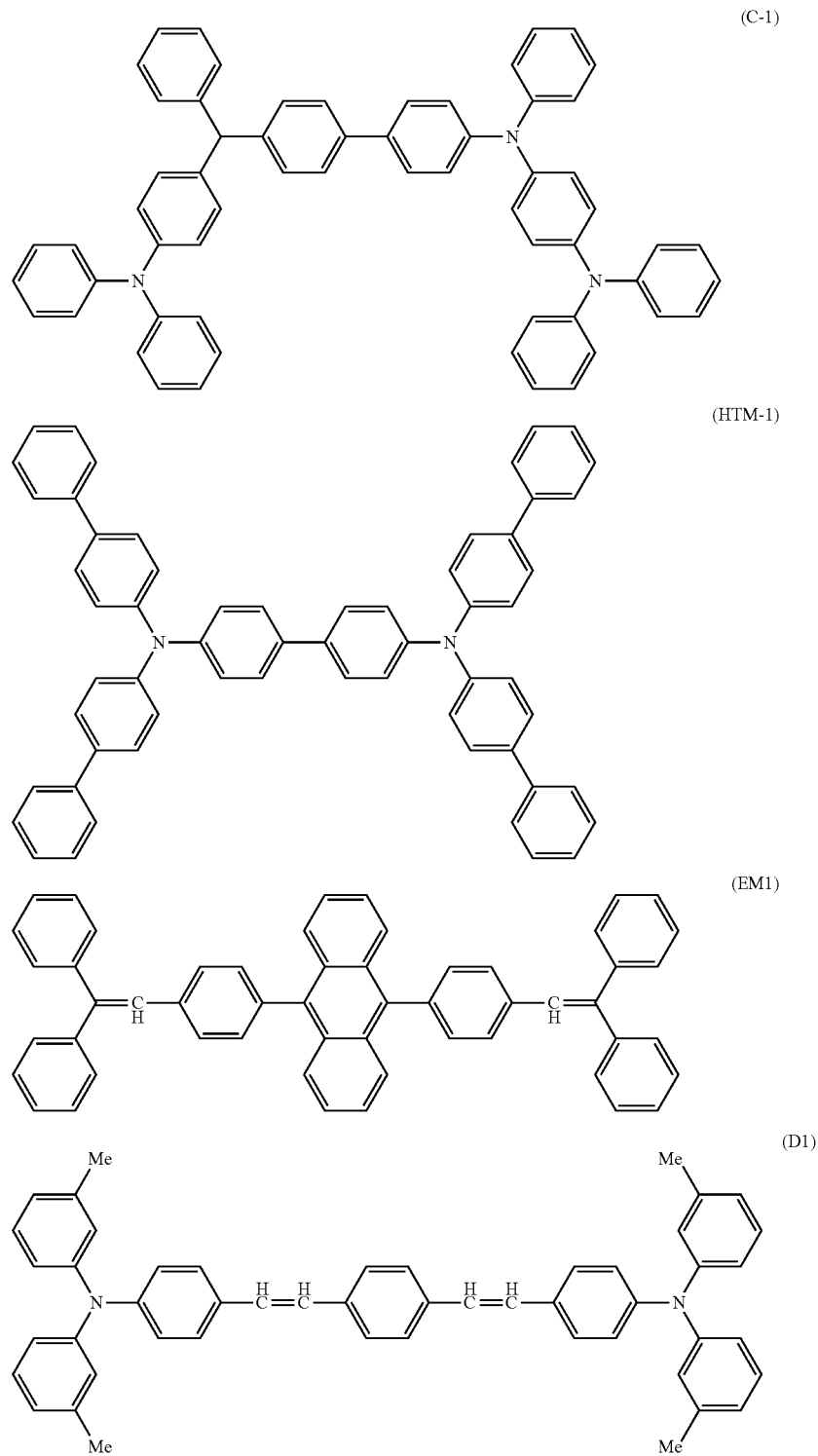

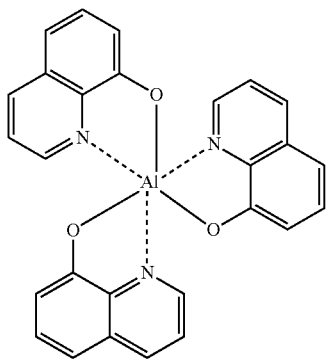
(Alq)

The organic EL device was evaluated by measuring a driving voltage at a current density of 10 mA/cm² and a half life of luminance at an initial luminance of 1,000 nits, at room temperature, and with a DC constant power supply. The results obtained are shown in Table 1.

Example 7

An organic EL device was fabricated and evaluated in the same manner as in Example 6, except that only the compound (A-1) which had been synthesized in Example 1 was used in the hole-injecting layer, the thickness thereof was rendered 10 nm, and the thickness of the hole-transporting layer (HTM-1) was changed to 70 nm. The results obtained are shown in Table 1.

Example 8

An organic EL device was fabricated and evaluated in the same manner as in Example 6, except that only the compound (A-7) which had been synthesized in Example 4 was used in the hole-injecting layer, the thickness thereof was rendered 10 nm, and the thickness of the hole-transporting layer (HTM-1) was changed to 70 nm. The results obtained are shown in Table 1.

Example 9

An organic EL device was fabricated and evaluated in the same manner as in Example 6, except that only the compound (A-33) which had been synthesized in Example 5 was used in the hole-injecting layer, the thickness thereof was rendered 10 nm, and the thickness of the hole-transporting layer (HTM-1) was changed to 70 nm. The results obtained are shown in Table 1.

Example 10

An organic EL device was fabricated and evaluated in the same manner as in Example 6, except that the mixture of the compound (B-1) and the compound (B-3) which had been synthesized in Example 3 was used instead of the compound (A-21). The results obtained are shown in Table 1.

Comparative Example 1

An organic EL device was fabricated and evaluated in the same manner as in Example 6, except that the hole-injecting layer was formed using only the compound shown by the formula (C-1).

The results obtained are shown in Table 1.

Comparative Example 2

An organic EL device was fabricated in the same manner as in Example 6, except that the hole-injecting layer was formed by using only 2,7-difluoroindenodione shown by the formula (R-1), the thickness thereof was rendered 10 nm and the thickness of the hole-transporting layer (HTM-1) was changed to 70 nm. The resulting organic EL device suffered a significant degree of current leakage and could not give uniform emission. The reason is considered to be the influence of the crystallization of the compound (R-1) and the shortage of the acceptor due to the quinone structure. The results obtained are shown in Table 1.

TABLE 1

| | Hole-injecting layer constituent material | Driving voltage (V) | Half life (hr) |
|---|---|---|---|
| Example 6 | Compound (A-21) Compound (C-1) | 6.2 | 6,500 |
| Example 7 | Compound (A-1) | 5.9 | 6,800 |
| Example 8 | Compound (A-7) | 5.8 | 7,500 |
| Example 9 | Compound (A-33) | 5.7 | 7,600 |
| Example 10 | Compound (B-1) Compound (B-3) Compound (C-1) | 6.3 | 6,400 |
| Com. Ex. 1 | Compound (C-1) | 6.6 | 5,000 |
| Com. Ex. 2 | Compound (R-1) | Significant leakage | — |

INDUSTRIAL APPLICABILITY

The azaindenofluorenedione derivative of the invention is suitable as a material for an organic EL device.

The material for an organic EL device of the invention is suitable as a constituent material of an organic EL device, in particular, a hole-transporting layer or a hole-injecting layer.

The material for an organic EL device of the invention can also be used as a charge-transporting material of an electrophotographic photoreceptor.

The organic EL device of the invention can be suitably used as a light source such as a planar luminous body and backlight of a display, a display part of a portable phone, PDA, a car navigator, or an instruction panel of an automobile, an illuminator, and the like.

The contents of the above-described documents are herein incorporated by reference in its entirety.

The invention claimed is:

1. A material for an organic electroluminescence device, said material having a reduction potential of −1.0V (vsFC+/Fc; Fc refers to a ferrocene) or more in an acetonitrile solution and comprising an azaindenofluorenedione derivative shown by the following formula (I), (IIa) or (IIb):

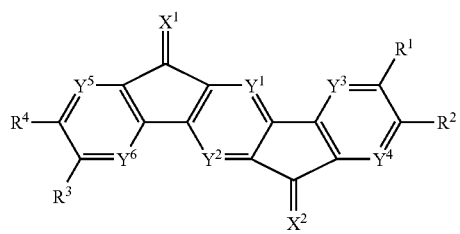
(I)

wherein $X^1$ and $X^2$, which may be the same or different, are one of the following divalent groups (a) to (g); $Y^1$ and $Y^2$ are independently —N= or —CH=, $Y^3$ to $Y^6$ are independently —N= or —CR= and at least one of $Y^1$ to $Y^6$ is —N=; $R^1$ to $R^4$ and R, which may be the same or different, are a hydrogen atom, a substituted or unsubstituted alkyl group, a substituted or unsubstituted aryl group, a substituted or unsubstituted heterocyclic group, a halogen atom, a substituted or unsubstituted alkoxy group, a substituted or unsubstituted aryloxy group or a cyano group; and $R^1$ and $R^2$, or $R^3$ and $R^4$ may be bonded to each other to form a ring, respectively;

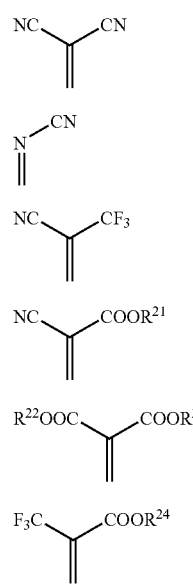

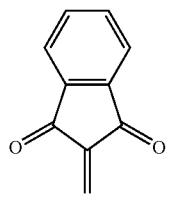
(g)

wherein $R^{21}$ to $R^{24}$, which may be the same or different, are a hydrogen atom, a substituted or unsubstituted alkyl group, a substituted or unsubstituted aryl group, or a substituted or unsubstituted heterocyclic group; and $R^{22}$ and $R^{23}$ may be bonded to each other to form a ring;

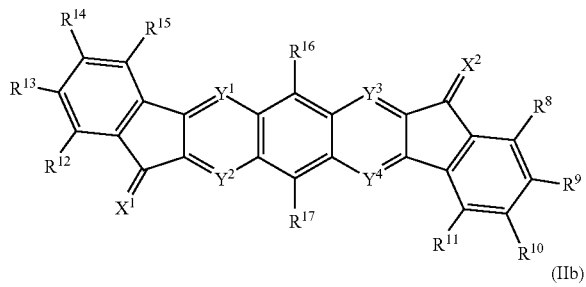

wherein $X^1$ and $X^2$ are the same as $X^1$ and $X^2$ in the formula (I); $Y^1$ to $Y^4$ are independently —N= or —CH=, and at least one of $Y^1$ to $Y^4$ is —N=; $R^8$ to $R^{17}$ may be the same or different, and $R^8$ to $R^{17}$ are a hydrogen atom, a substituted or unsubstituted alkyl group, a substituted or unsubstituted aryl group, a substituted or unsubstituted heterocyclic group, a halogen atom, a substituted or unsubstituted alkoxy group, a substituted or unsubstituted aryloxy group or a cyano group; and adjacent groups of $R^8$ to $R^{11}$ or $R^{12}$ to $R^{15}$ may be bonded to each other to form a ring.

2. The material for an organic electroluminescence device of claim 1, which has a reduction potential of −0.8V (vsFC+/Fc; Fc refers to a ferrocene) or more in an acetonitrile solution.

3. The material for an organic electroluminescence device of claim 2, which is a hole-injecting material.

4. An organic electroluminescence device comprising an anode, a cathode and an organic thin film layer therebetween; the organic thin film layer being a multilayer stack wherein a hole-injecting layer, a hole transporting layer, an emitting layer and an electron transporting layer are stacked in this order from the anode; and the hole-injecting layer comprising the material for an organic electroluminescence device of claim 2.

5. The material for an organic electroluminescence device of claim 2, comprising an azaindenofluorenedione derivative of formula (I).

6. The material for an organic electroluminescence device of claim 2, comprising an azaindenofluorenedione derivative of formula (IIa).

7. The material for an organic electroluminescence device of claim 2, comprising an azaindenofluorenedione derivative of formula (IIb).

8. The material for an organic electroluminescence device of claim 1, which is a hole-injecting material.

9. An organic electroluminescence device comprising an anode, a cathode and an organic thin film layer therebetween;
the organic thin film layer being a multilayer stack wherein a hole-injecting layer, a hole transporting layer, an emitting layer and an electron transporting layer are stacked in this order from the anode; and
the hole-injecting layer comprising the material for an organic electroluminescence device of claim 1.

10. The material for an organic electroluminescence device of claim 1, comprising an azaindenofluorenedione derivative of formula (I).

11. The material for an organic electroluminescence device of claim 1, comprising an azaindenofluorenedione derivative of formula (IIa).

12. The material for an organic electroluminescence device of claim 1, comprising an azaindenofluorenedione derivative of formula (IIb).

* * * * *